US006512577B1

(12) United States Patent
Ozanich

(10) Patent No.: US 6,512,577 B1
(45) Date of Patent: Jan. 28, 2003

(54) APPARATUS AND METHOD FOR MEASURING AND CORRELATING CHARACTERISTICS OF FRUIT WITH VISIBLE/NEAR INFRA-RED SPECTRUM

(76) Inventor: Richard M. Ozanich, 3100 George Washington Way, Suite 104, Richland, WA (US) 99352

( * ) Notice: Subject to any disclaimer, the term of this patent is extended or adjusted under 35 U.S.C. 154(b) by 0 days.

(21) Appl. No.: 09/524,329

(22) Filed: Mar. 13, 2000

(51) Int. Cl.[7] ............................ G01J 3/42; G01N 21/47; G01N 21/25
(52) U.S. Cl. ................... 356/73; 356/326; 356/402; 250/910; 209/588
(58) Field of Search .................... 356/73, 326, 328, 356/402; 250/910; 209/588

(56) References Cited

U.S. PATENT DOCUMENTS

| | | | |
|---|---|---|---|
| 4,883,953 A | 11/1989 | Koashi et al. ............... 250/226 |
| 5,089,701 A | 2/1992 | Dull et al. .................. 250/341 |
| 5,303,026 A | * 4/1994 | Strobl et al. ................ 356/318 |
| 5,324,945 A | 6/1994 | Iwamoto et al. ........ 250/339.01 |
| 5,708,271 A | 1/1998 | Ito et al. ................ 250/339.11 |
| 5,845,002 A | * 12/1998 | Heck et al. .................. 209/588 |
| 5,926,262 A | * 7/1999 | Jung et al. ..................... 356/73 |

* cited by examiner

Primary Examiner—F. L. Evans
(74) Attorney, Agent, or Firm—Liebler, Ivey & Connor; Floyd E. Ivey

(57) ABSTRACT

This disclosure is of 1) the utilization of the spectrum from 250 nm to 1150 nm for measurement or prediction of one or more parameters, e.g., brix, firmness, acidity, density, pH, color and external and internal defects and disorders including, for example, surface and subsurface bruises, scarring, sun scald, punctures, in N—H, C—H and O—H samples including fruit; 2) an apparatus and method of detecting emitted light from samples exposed to the above spectrum in at least one spectrum range and, in the preferred embodiment, in at least two spectrum ranges of 250 to 499 nm and 500 nm to 1150 nm; 3) the use of the chlorophyl band, peaking at 680 nm, in combination with the spectrum from 700 nm and above to predict one or more of the above parameters; 4) the use of the visible pigment region, including xanthophyll, from approximately 250 nm to 499 nm and anthocyanin from approximately 500 to 550 nm, in combination with the chlorophyl band and the spectrum from 700 nm and above to predict the all of the above parameters.

20 Claims, 22 Drawing Sheets

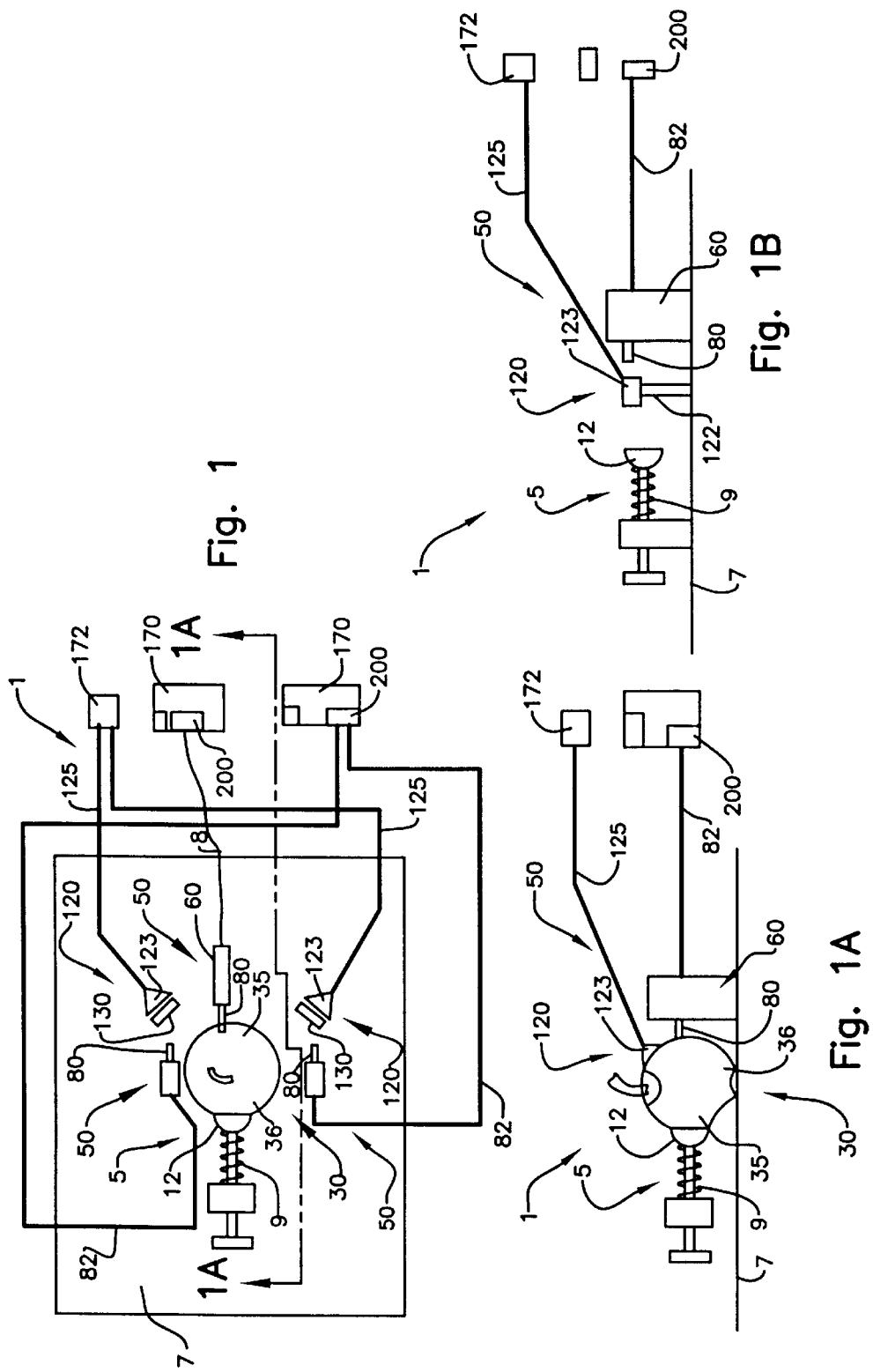

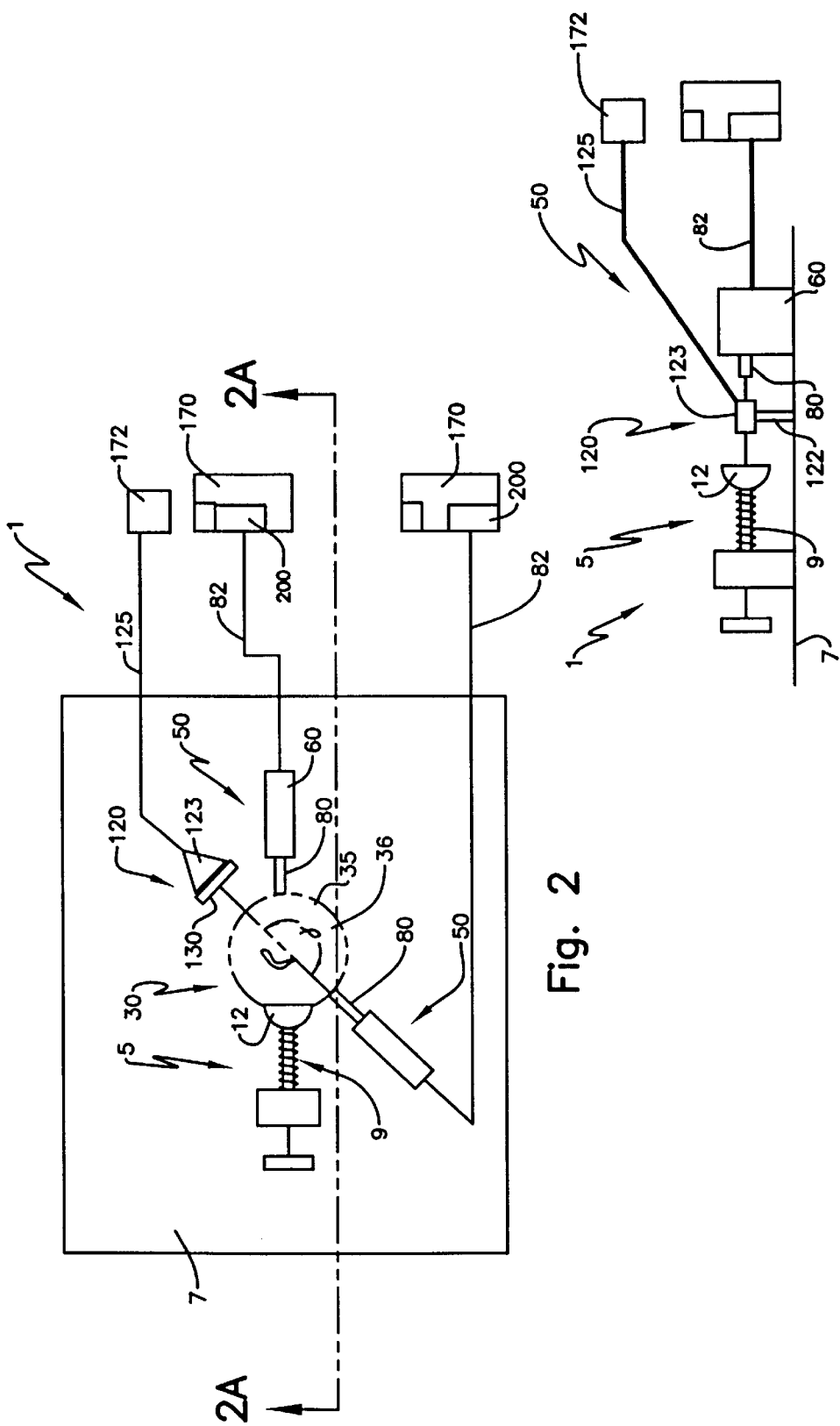

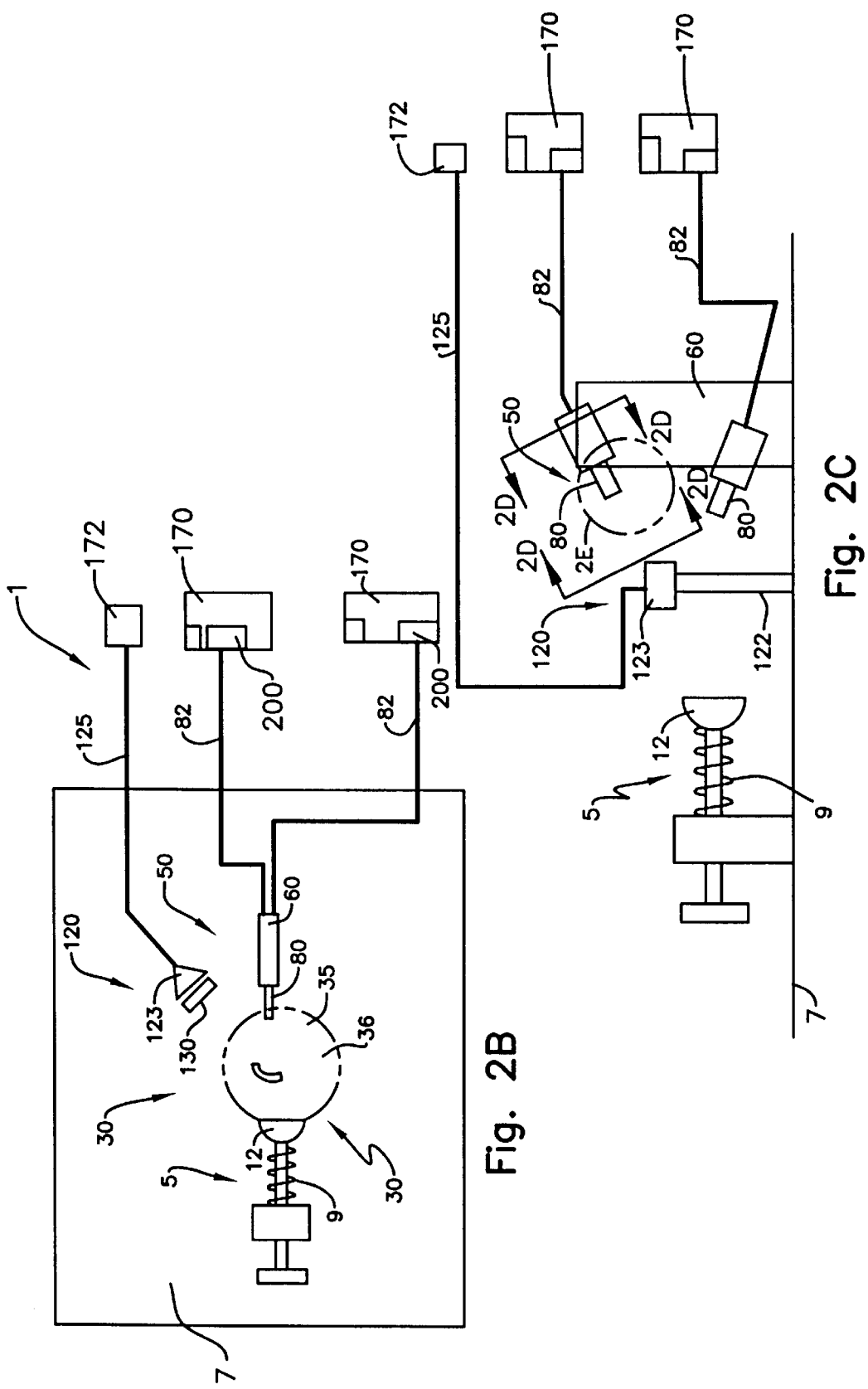

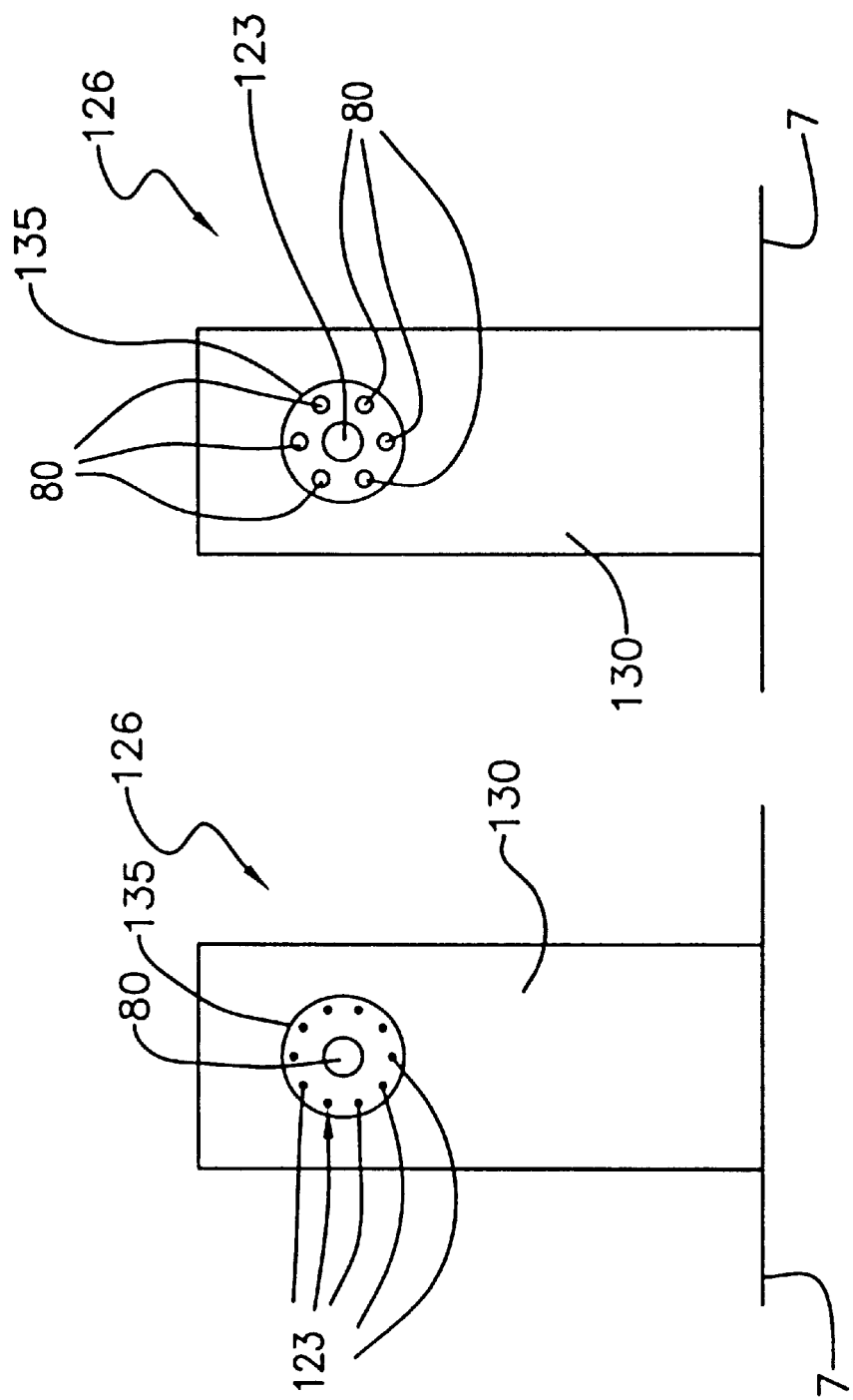

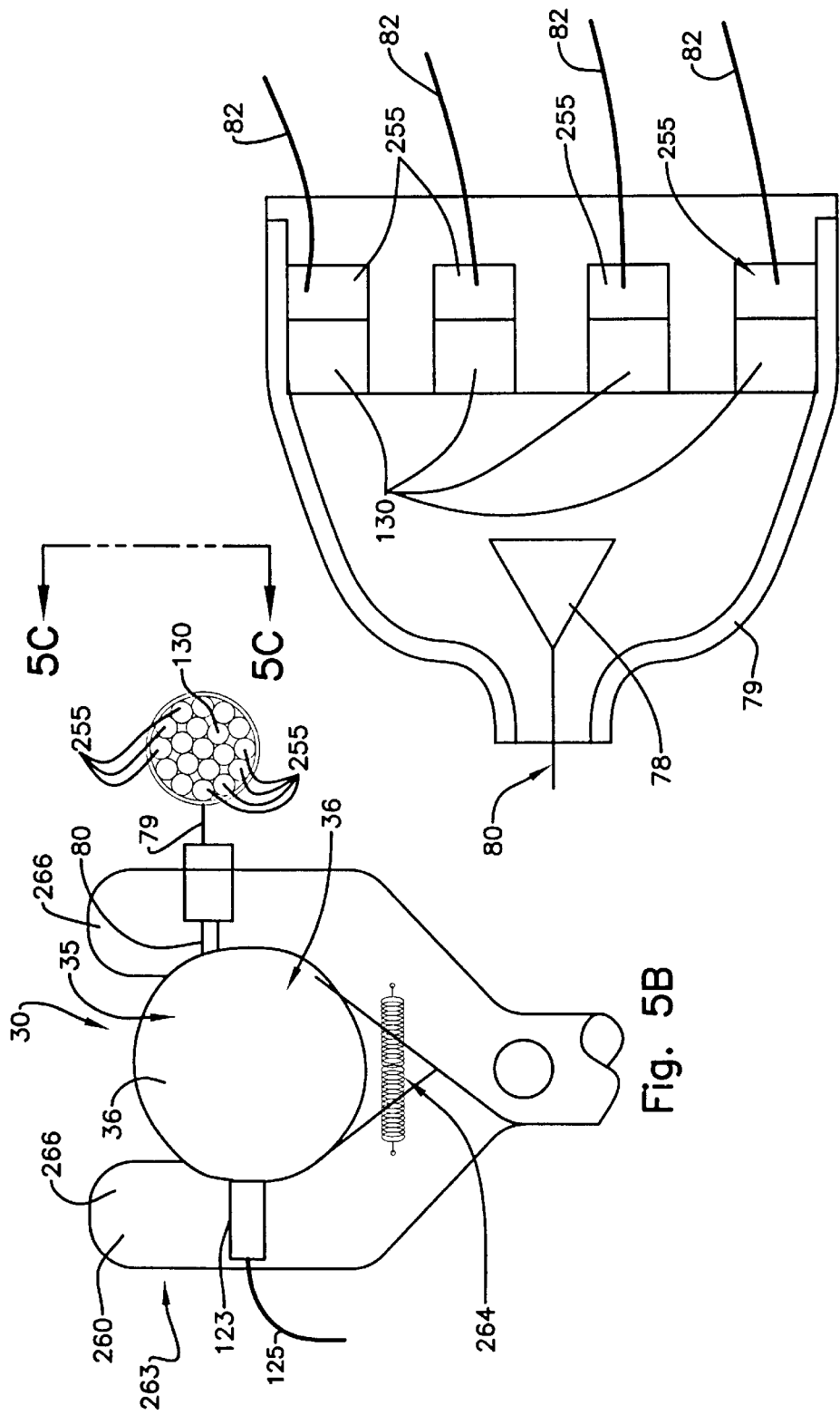

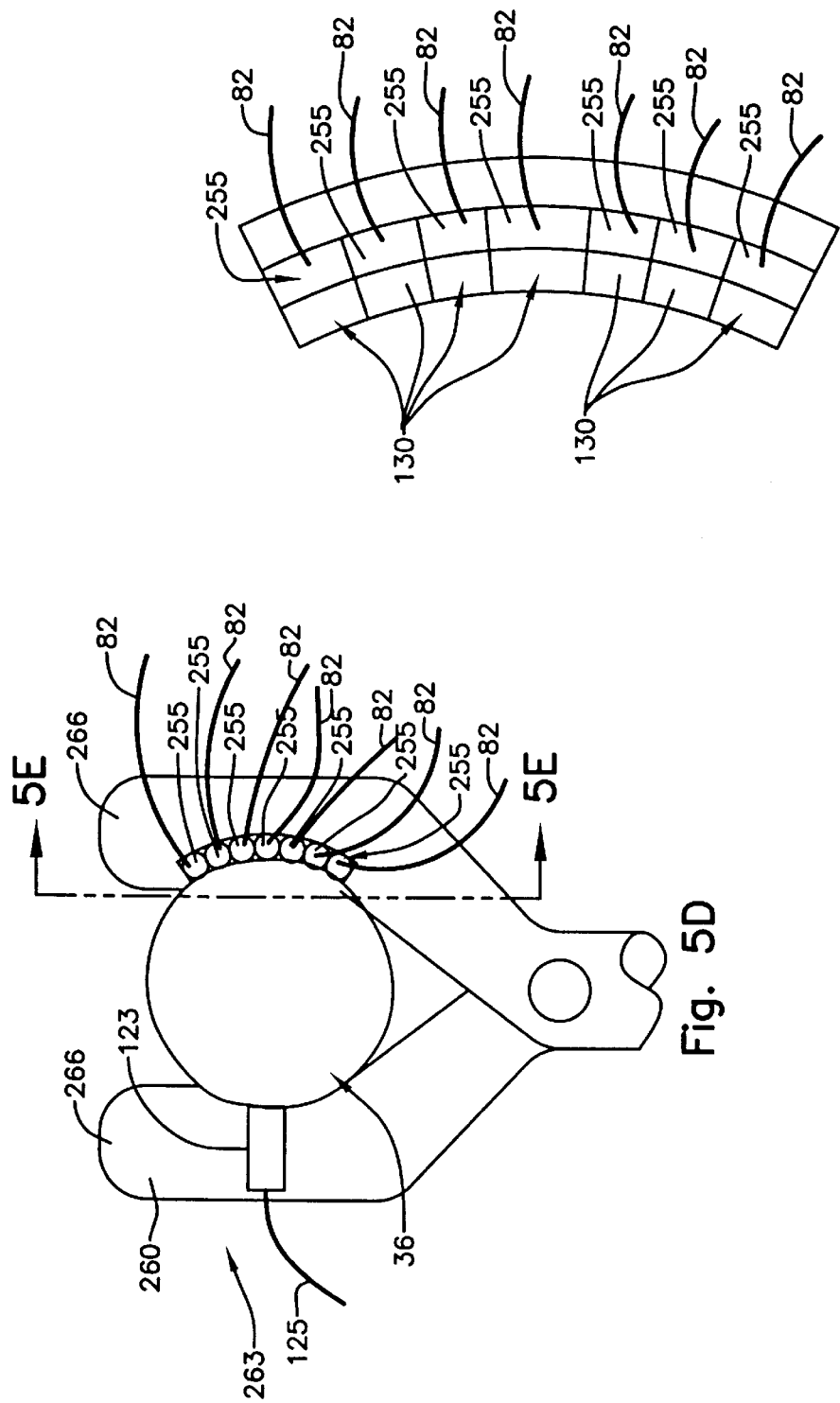

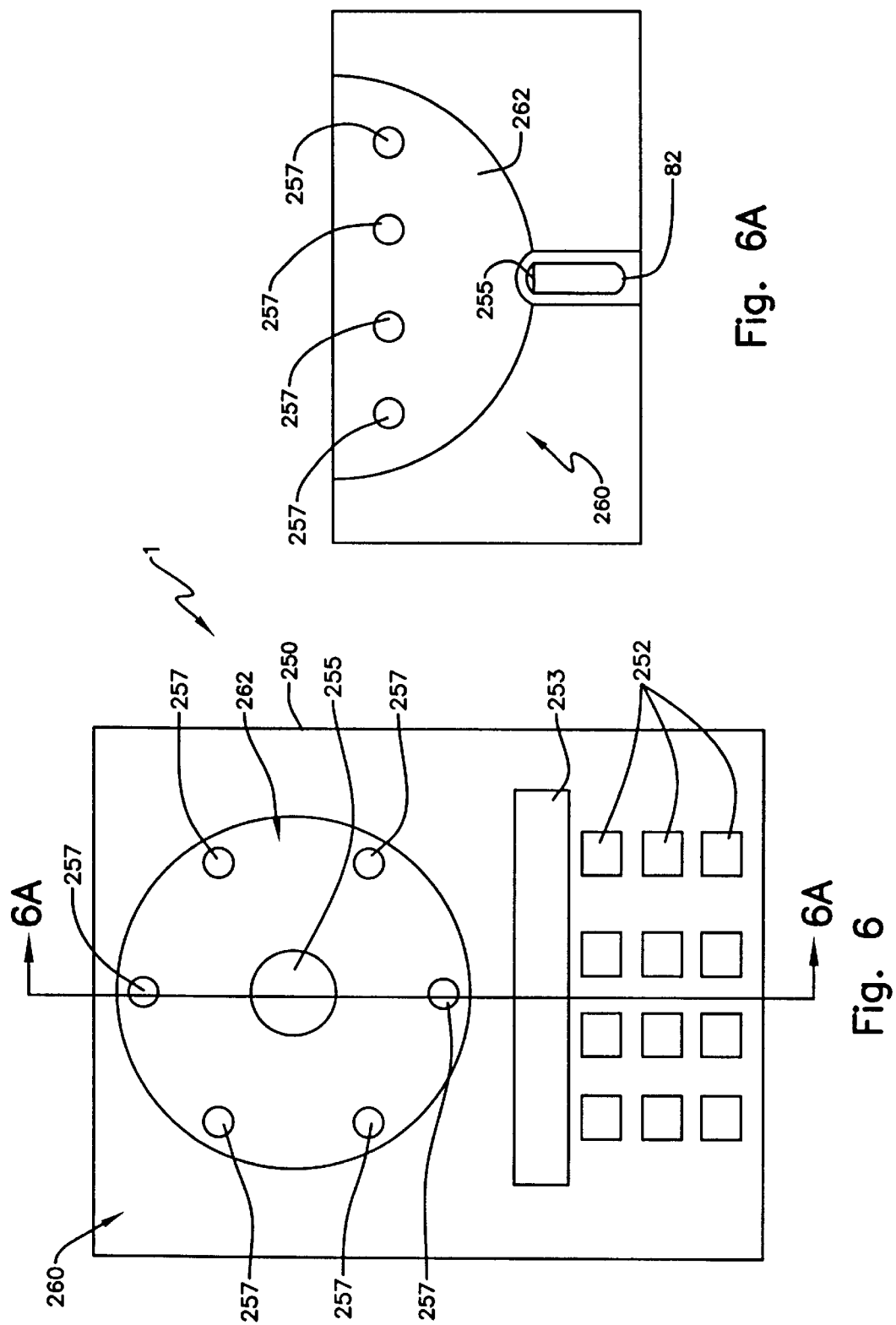

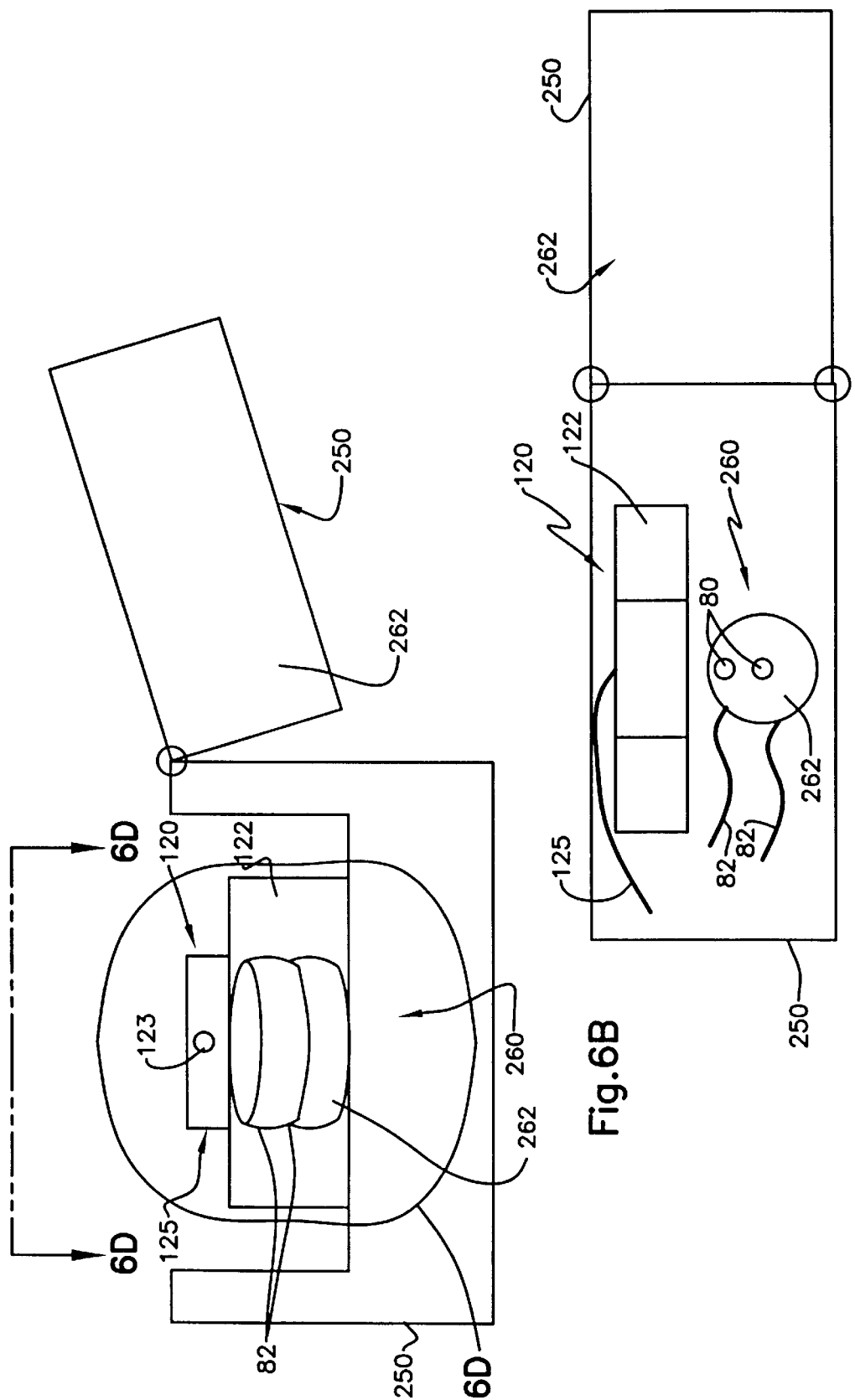

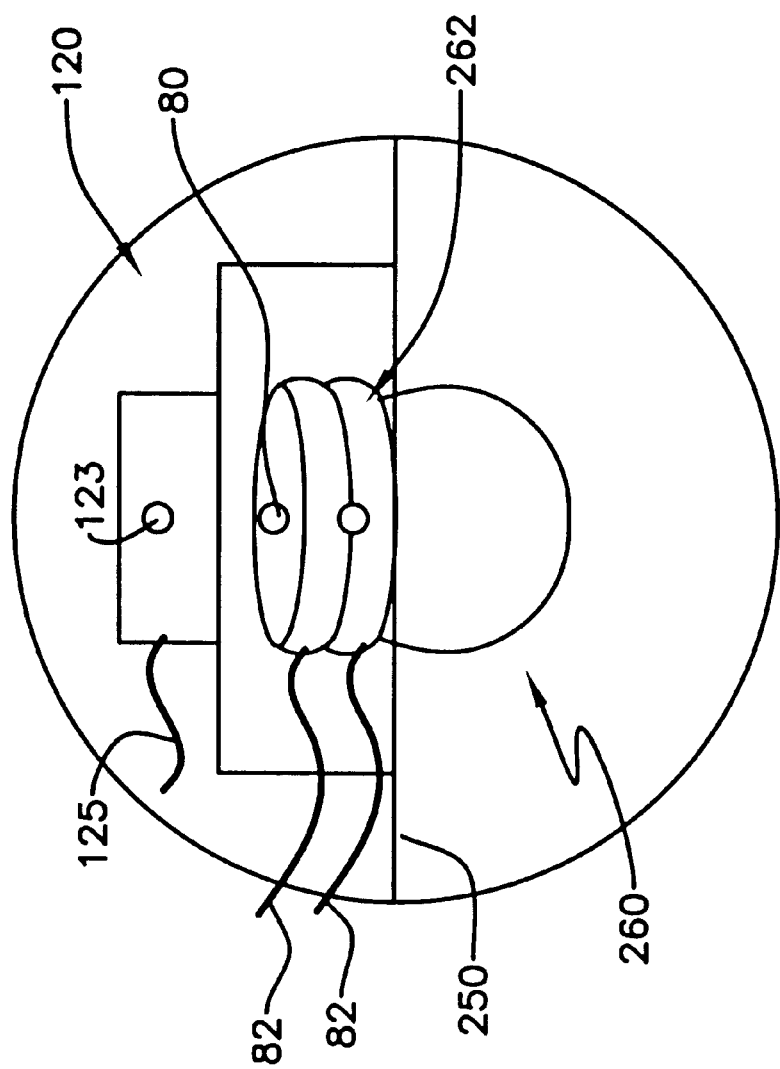

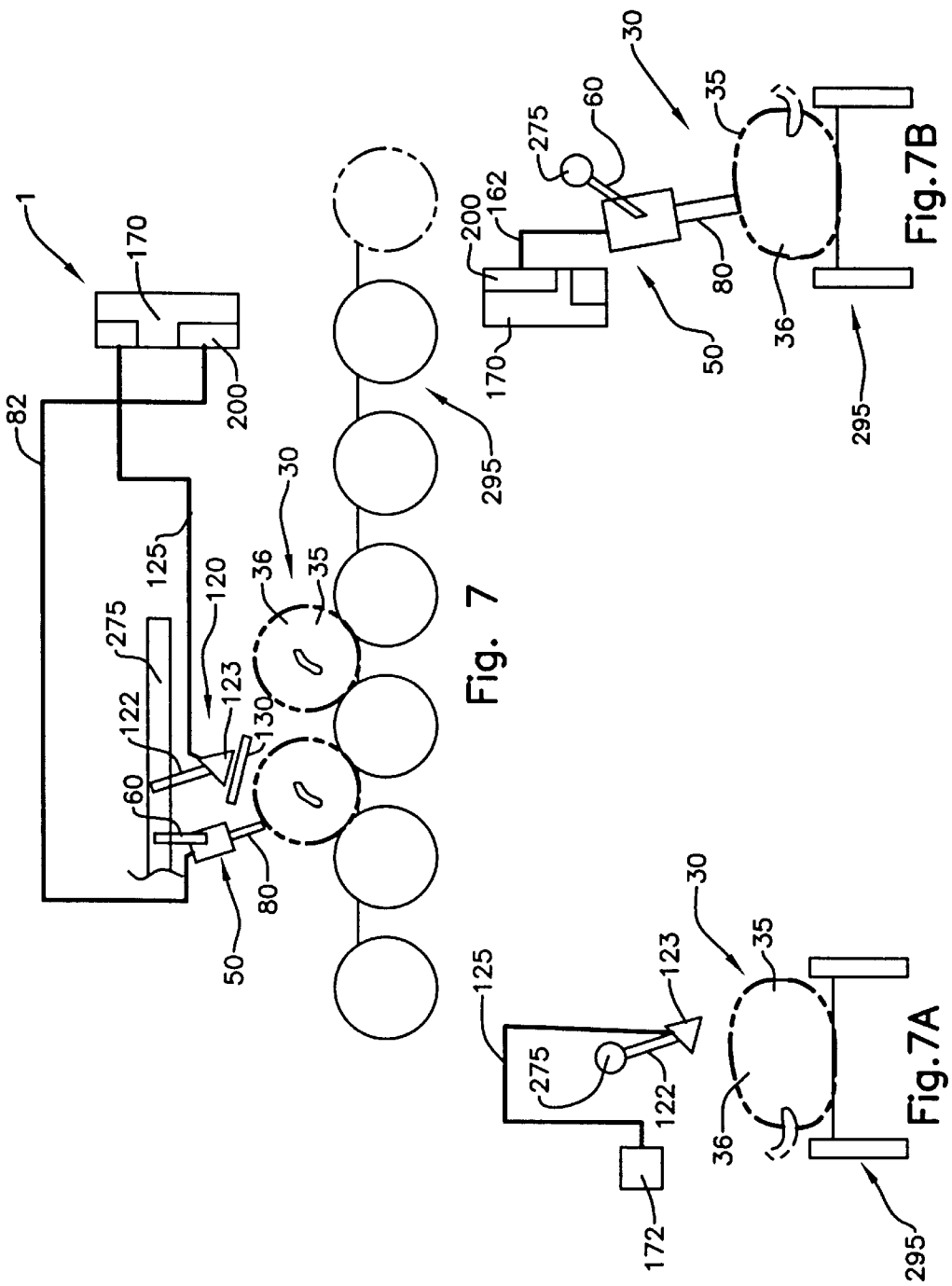

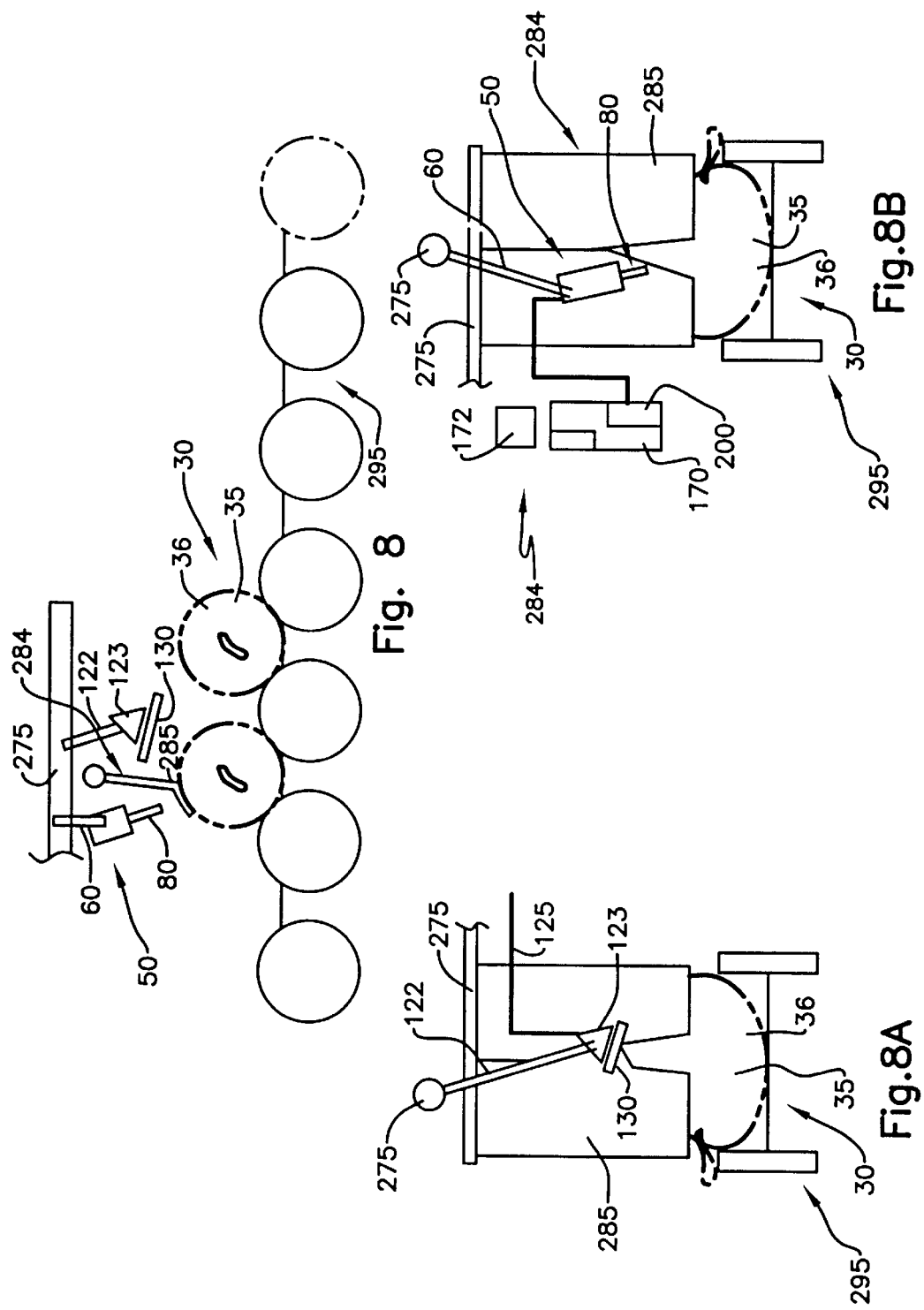

APPARATUS AND METHOD FOR MEASURING AND CORRELATING CHARACTERISTICS OF FRUIT WITH VISIBLE/NEAR INFRA-RED SPECTRUM

FIELD OF THE INVENTION

The present disclosure relates generally to the use of the combined visible and near infra red spectrum in an apparatus and method for measuring physical parameters, e.g., firmness, density and internal and external disorders, and chemical parameters, e.g., molecules containing O—H, N—H and C—H chemical bonds, in fruit and correlating the resulting measurements with fruit quality and maturity characteristics, including Brix, acidity, density, pH, firmness, color and internal and external defects to forecast consumer preferences including taste preferences and appearance, as well as harvest, storage and shipping variables. With the present apparatus and method, the interior of a sample, e.g., fruit including apples, is illuminated and the spectrum of absorbed and scattered light from the sample is detected and measured. Prediction, calibration and classification algorithms are determined for the category of sample permitting correlation between the spectrum of absorbed and scattered light and sample characteristics, e.g., fruit quality and maturity characteristics.

BACKGROUND OF THE INVENTION

The embodiments disclosed herein has a focus on combined visible and near-infrared (NIR) spectroscopy and its modes of use, major issues in the application of NIR to the measurement of O—H, N—H and C—H containing molecules that are indicators of sample quality including fruit quality and in particular tree fruit quality.

Near-Infrared Spectroscopy Background: Near-infrared spectroscopy has been used since the 1970's for the compositional analysis of low moisture food products. However, only in the last 10–15 years has NIR been successfully applied to the analysis of high moisture products such as fruit. NIR is a form of vibrational spectroscopy that is particularly sensitive to the presence of molecules containing C—H (carbon-hydrogen), O—H (oxygen-hydrogen), and N—H (nitrogen-hydrogen) groups. Therefore, constituents such as sugars and starch (C—H), moisture, alcohols and acids (O—H), and protein (N—H) can be quantified in liquids, solids and slurries. In addition, the analysis of gases (e.g., water vapor, ammonia) is possible. NIR is not a trace analysis technique and it is generally used for measuring components that are present at concentrations greater than 0.1%.

Short-Wavelength NIR vs. Long-Wavelength NIR: NIR has traditionally been carried out in the 1100–2500 nm region of the electromagnetic spectrum. However, the wavelength region of ~700–1100 nm (short wavelength-NIR or SW-NIR) has been gaining increased attention. The SW-NIR region offers numerous advantages for on-line and in-situ bulk constituent analysis. This portion of the NIR is accessible to low-cost, high performance silicon detectors and fiber optics. In addition, high intensity laser diodes and low-cost light emitting diodes are becoming increasingly available at a variety of NIR wavelength outputs.

The relatively low extinction (light absorption) coefficients in the SW-NIR region yields linear absorbance with analyte concentration and permits long, convenient pathlengths to be used. The depth of penetration of SW-NIR is also much greater than that of the longer wavelength NIR, permitting a more adequate sampling of the "bulk" material. This is of particular importance when the sample to be analyzed is heterogeneous such as fruit.

Diffuse Reflectance Sampling vs. Transmission Sampling: Traditional NIR analysis has used diffuse reflectance sampling. This mode of sampling is convenient for samples that are highly light scattering or samples for which there is no physical ability to employ transmission spectroscopy. Diffusely reflected light is light that has entered a sample, undergone multiple scattering events, and emerged from the surface in random directions. A portion of light that enters the sample is also absorbed. The depth of penetration of the light is highly dependent on the sample characteristics and is often affected by the size of particles in the sample and the sample density. Furthermore, diffuse reflectance is biased to the surface of a sample and may not provide representative data for large heterogeneous samples such as apples.

While transmission sampling is typically used for the analysis of clear solutions, it also can be used for interrogating solid samples. A transmission measurement is usually performed with the detector directly opposite the light source (i.e., at 180 degrees) and with the sample in the center. Alternately the detector can be placed closer to the light source (at angles less than 180 degrees), which is often necessary to provide a more easily detected level of light. Because of the long sample pathlengths and highly light scattering nature of most tree fruit, transmission measurements can only be performed in the SW-NIR wavelength region, unless special procedures are employed to improve signal to noise.

NIR Calibration: NIR analysis is largely an empirical method; the spectral lines are difficult to assign, and the spectroscopy is frequently carried out on highly light scattering samples where adherence to Beer's Law is not expected. Accordingly, statistical calibration techniques are often used to determine if there is a relationship between analyte concentration (or sample property) and instrument response. To uncover this relationship requires a representative set of "training" or calibration samples. These samples must span the complete range of chemical and physical properties of all future samples to be seen by the instrument.

Calibration begins by acquiring a spectrum of each of the samples. Constituent values for all of the analytes of interest are then obtained using the best reference method available with regards to accuracy and precision. It is important to note that a quantitative spectral method developed using statistical correlation techniques can perform no better than the reference method.

After the data has been acquired, computer models employing statistical calibration techniques are developed that relate the NIR spectra to the measured constituent values or properties. These calibration models can be expanded and must be periodically updated and verified using conventional testing procedures.

Factors affecting calibration include fruit type and variety, seasonal and geographical differences, and whether the fruit is fresh or has been in cold or other storage. Calibration variables include the particular properties or analytes to be measured and the concentration or level of the properties. Intercorrelations (co-linearity) should be minimized in calibration samples so as not to lead to false interpretation of a models predictive ability. Co-linearity occurs when the concentrations of two components are correlated, e.g., an inverse correlation exists when one component is high, the other is always low or vice versa.

Application of NIR to Tree Fruit and Existing On-Line NIR Instrumentation: A growing body of research exists for NIR analysis of tree fruit. NIR has been used for the measurement of fruit juice, flesh, and whole fruit. In juice, the individual sugars (sucrose, fructose, glucose) and total acidity can be quantified with high correlation (>0.95) and acceptable error. Individual sugars can not be readily measured in whole fruit. Brix is the most successfully measured NIR parameter in whole fruit and can generally be achieved with an error of ±0.5–1.0 Brix. More tentative recent research results indicate firmness and acidity measurement in whole fruit also may be possible.

Only in Japan has the large-scale deployment of on-line NIR for fruit sorting occurred. These instruments require manual placement/orientation of the fruit prior to measurement and early versions were limited to a measurement rate of three samples per second. The Japanese NIR instruments are also limited to a single lane of fruit and appear to be difficult to adapt to multi-lane sorting equipment used in the United States of America. While earlier Japanese NIR instruments employed reflectance sampling, more recent instruments use transmission sampling.

In Koashi et al., U.S. Pat. No. 4,883,953, there is described a method and apparatus for measuring sugar concentrations in liquids. Measurements are made at two different depths using weak and strong infrared radiation. The level of sugar at depths between these two depths can then be measured. The method and apparatus utilizes wavelength bands of 950–1,150 nm, 1,150–1,300 nm, and 1,300–1,450 nm.

U.S. Pat. No. 5,089,701, to Dull et al., uses near infrared (NIR) radiation in the wavelength range of 800–1,050 nm to demonstrate measurement of soluble solids in Honeydew melons. An eight-centimeter or greater distance between the light delivery location to the fruit and the light collection location was found to be necessary to accurately predict soluble solids because of the thick rind.

Iwamoto et al., U.S. Pat. No. 5,324,945, also use NIR radiation to predict sugar content of mandarin oranges. Iwamoto utilizes a transmission measurement arrangement whereby the light traverses through the entire sample of fruit and is detected at 180 degrees relative to the light input angle. Moderately thick-skinned fruit (mandarin oranges) were used to demonstrate the method, which relies on a fruit diameter correction by normalizing (dividing) the spectra at 844 nm, where, according to the disclosed data, correlation with the sugar content is lowest. NIR wavelengths in the range of 914–919 nm were found to have the highest correlation with sugar content. Second, third and fourth wavelengths that were added to the multiple regression analysis equation used to correlate the NIR spectra with sugar content were 769–770 nm, 745 nm, and 785–786 nm.

In U.S. Pat. No. 5,708,271, Ito et al. demonstrates a sugar content measuring apparatus that utilizes three different NIR wavelengths in the range from 860–960 nm. The angle between fight delivery and collection was varied between 0 and 180 degrees and it was concluded that the low NIR radiation levels that must be detected when a photo-detector is placed at 180 degrees relative to the radiation source are not desirable because of the more complicated procedures and equipment that are required. A correlation of NIR absorbance with sugar content of muskmelons and watermelons was found when an intermediate angle, which gave greater NIR radiation intensity, was detected. No size correction was necessary with this approach.

U.S. Pat. No. 4,883,953 to Koashi et al. uses comparatively long wavelengths of NIR radiation (i.e., >950 nm), while in U.S. Pat. No. 5,089,701 to Dull, and U.S. Pat. No. 5,708,271 to Ito, wavelengths of NIR radiation used are greater than 800 nm and 860 nm, respectively. In U.S. Pat. No. 5,324,945 to Iwamoto, the wavelengths of NIR radiation with the highest correlation to sugar content of mandarins were 914 nm or 919 nm, when the fruit were measured on the equatorial or stem portion, respectively.

All of these methods use near-infrared wavelengths of light to correlate with sugar content of whole fruit. No other quality parameters are measured by these techniques.

The four disclosed patents are similar to the apparatus and method described here in that the present disclosure also measures sugar content. Two of the patents (U.S. Pat. Nos. 5,089,701 and 5,324,945) NIR wavelengths less than 850 nm) U.S. Pat. No. 5,089,701 discloses the operation of the invention within the range of "from about 800 nanometers to about 1050 nanometers." U.S. Pat. No. 5,324,945 lists 914 nm or 919 nm as the primary analytical wavelength correlated with whole fruit sugar content; multiple linear regression was used to add successive wavelengths to the model as follows: 769–770 nm (2nd wavelength added), 745 nm (3rd wavelength added), and 785–786 nm (4th wavelength added). In U.S. Pat. No. 5,089,701, addition of the fourth wavelength to the model only reduced the standard error of prediction (SEP) by 0.1–0.2 Brix, which is approaching or less than the error limits of the refractometer used to determine the reference ("true") Brix values.

Other similarities between the method and apparatus described herein with the four patents listed above include the use of multivariate statistical analysis to establish correlation of the near-infrared spectral data with sugar content of whole fruit. Most also use data processing techniques such as second derivative transformation and some type of spectral normalization. All of these methods for relating NIR spectra to chemical or physical properties are well known to those practiced in the art of NIR spectroscopy.

The foregoing patents and printed publications are provided herewith in an Information Disclosure Statement in accordance with 37 CFR 1.97.

SUMMARY OF THE INVENTION

Research groups around the world continue to explore the applications of near infrared spectroscopy to tree fruit. The apparatus and process disclosed herein is of the nondestructive determination or prediction of O—H, N—H and C—H containing molecules that are indicators of sample qualities, including fruit such as apples, cherries, oranges, grapes, potatoes, cereals, and other such samples, using near infrared spectroscopy. Prior art has utilized spectrum from 745 nm and above. This disclosure is of 1) the utilization of the spectrum from 250 nm to 1150 nm for measurement or prediction of one or more parameters, e.g., Brix, firmness, acidity, density, pH, color and external and internal defects and disorders including, for example, surface and subsurface bruises, scarring, sun scald, punctures, watercore, internal browning, in samples including fruit; 2) an apparatus and method of illuminating the interior of a sample and detecting emitted light from samples exposed to the above spectrum in at least one spectrum range and, in the preferred embodiment, in at least two spectrum ranges of 250 to 499 nm and 500 nm to 1150 nm; 3) the use of the chlorophyl absorption band, pealing at 680 nm, in combination with the spectrum from 700 nm and above to predict one or more of the above parameters; 4) the use of the visible pigment region, including xanthophyll, from approximately 250 nm to 499 nm and anthocyanin from approximately 500 to 550 nm, in combination with the chlorophyl band and the spectrum from 700 nm and above to predict the all of the above parameters.

Prior art has only examined spectrum from fruit for the prediction of Brix. This disclosure is of the examination of a greater spectrum using the combined visible and near infrared wavelength regions for the prediction of the above stated characteristics. The apparatus and method disclosed eliminates the problem of saturation of light spectrum detectors within particular spectrum regions while gaining data within other regions in the examination, in particular, of fruit. That is, spectrometers with CCD (charge coupled device) array or PDA (photodiode array) detectors will detect light within the 250 to 1150 nm region, but when detecting spectrum out of fruit will saturate in regions, e.g., 700 to 925 nm, or the signal to noise (S/N) ratio will be unsatisfactory and not useful for quantitation in other regions, e.g., 250 to 699 nm and greater than 925 nm, thus precluding the gaining of additional information regarding the parameters above stated. Thus disclosed herein is an apparatus and method permitting 1) the automated measurement of multiple spectra with a single pass or single measurement activity by detecting more than one spectrum range during a single pass or single measurement activity, 2) combining the more than one spectrum range detected, 3) comparing the combined spectrum with a stored calibration algorithm to 4) predicting the parameters above stated.

In each instance in the method and apparatus disclosed herein there will be a dual or plural spectrum acquisition from a sample from different spectrum regions. This is accomplished by 1) serially acquiring data from different spectrum regions using different light source intensities or different detector/spectrometer exposure times using a single spectrometer; 2) acquiring data in parallel with multiple spectrometers using different light intensities, e.g., by varying the voltage input to a lamp, or different exposure times to the spectrometers; however, different exposure times leads to sampling errors particularly where a sample is moving, e.g., in a processing line, due to viewing different regions on a sample; and 3) with multiple spectrometers using the same exposure time, constant lamp intensity with dual or a plurality of light detectors including neutral density filtered light detectors (where filtered light detectors giving the same effect as using a shorter exposure time). This approach provides dual or plural spectra with good signal to noise ratio for all wavelengths intensities using a single light source intensity and the same exposure time on all spectrometer detectors. This approach uses at least one filtered light detector using filtered input 82 to the spectrometer 170 rather than different exposure times. A filter can be any material that absorbs light with equal strength over the range of wavelengths used by the spectrometer including but not limited to neutral density filters, Spectralon, Teflon, opal coated glass, screen. The dual intensity approach using two different lamp voltages proves problematic because the high and low intensity spectra are not easily combined together due to slope differences in the spectra. The dual exposure approach yields excellent combined spectra, which are necessary for firmness and other characteristic prediction and also improves Brix prediction accuracy.

Measurements are disclosed, with the apparatus and process of this disclosure, which are made simultaneously in multiple sample types, e.g., where samples are apples, measurement is independent of a particular apple cultivar, using a single calibration equation with errors of ±1–2 lb. and ±0.5–1.0 Brix. This disclosure pertains to laboratory, portable and on-line NIR analyzers for the simultaneous measurement of multiple quality parameters of samples including fruit. Depending on the application or particular characteristic sought to be predicted or measured, a variety of calibration models may be used, from universal to highly specific, e.g., the calibration can be specific to a variety, different geographical location, stored v. fresh fruit and other calibrations.

Disclosed here is the greater role NIR technology will play as a tool for grading sample qualities including fruit quality. The unique ability of NIR statistical calibration techniques to extract non-chemical "properties" provides a technique for development of a general NIR "quality index" for tree fruit. This general "quality index" combines all of the information that could be extracted from the NIR spectra and includes information about Brix, acidity, firmness, density, pH, color and external and internal disorders and defects.

The near-infrared wavelength region below 745 nm has not been explored by prior investigations. Generally, the prior art design and or apparatus utilized was such that longer wavelength regions provided adequate data. The prior art for measuring sugar content in liquids and whole fruits using near-infrared spectroscopy utilizes longer wavelengths of radiation. No prior art exists for measuring other important quality parameters such as firmness, acidity, density and pH. No prior art has correlated consumer taste preferences with the combined NIR determination of multiple quality parameters such as sugar, acidity, pH, firmness, color, and internal and external defects and disorders.

It will be shown in this patent that the wavelength region from 250–1150 nm can be used to nondestructively measure not only sugar content (Brix) in various whole fruit, but firmness, density, acidity, pH, color and internal and external defects as well. For example, density of oranges is measured and is correlated to quality, e.g., freeze damaged fruit and dry fruit typically have lower density than good quality fruit and lower water content (i.e., greater dry matter content). NIR density measurement can be used to remove poor quality fruit in a sorting/packing line or at the supermarket. Information about color pigments and chlorophyll, related to maturity and quality, are obtained from 250 to approximately 699 nm. From approximately 700–1150 nm, the shortwavelength NIR region, C—H, N—H, O—H information is obtained. Combining the visible and NIR region gives more analytical power to predict chemical, physical and consumer properties, particularly for fruit. All of these parameters can be determined simultaneously from a combined visible/NIR spectrum. Multiple parameters can be combined to arrive at a "Quality Index" that is a better measure of maturity or quality than a single parameter.

Absorption of light by whole fruit in the approximately 250–699 nm region is dominated by pigments, including chlorophyll (a green pigment) which absorbs in the approximately 600–699 nm region. Chlorophyll is composed of a number of chlorophyll-protein complexes. Changes in these chlorophyll-protein complexes and changes in other pigments, most notably anthocyanin (red pigment) and xanthophylls (yellow pigments), are related to the maturation and ripening process. Chlorophyll and pigments are important for determining firmness.

While the NIR wavelengths of 700–925 nm and longer have been readily accessible to common near-infrared spectrometers, shorter wavelengths have not typically been explored for the following reasons: 1) lead-salt and other detector types, e.g., InGaAs, were not sensitive to shorter wavelengths; 2) light diffraction gratings were blazed at longer wavelengths yielding poor efficiency at short wavelengths; 3) light sources did not have enough energy output at shorter wavelengths to overcome the strong light absorption and scattering of biological (plant and animal) material in the visible region (250–699 nm).

Disclosed herein is an apparatus and method for measurement, with the visible/near-infrared (VIS/NIR) spectroscopic technique for sugar content (also known as Brix or soluble solids, which is inversely related to dry matter content), firmness, acidity, density, pH, color and internal and external defects and disorders. The apparatus and method is successful in measuring one or more such characteristic in apples, grapes, oranges, potatoes and cherries. Demonstrated in this disclosure is the ability to combine chemical and physical property data permitting the prediction of consumer properties, such as taste, appearance and color; harvest variables, such as time for harvest; and storage variables such as prediction of firmness retention and time until spoilage.

BRIEF DESCRIPTION OF THE DRAWINGS

The foregoing and other features and advantages of the present disclosure will become more readily appreciated as the same become better understood by reference to the following detailed description of the preferred embodiment and additional embodiments of the disclosure when taken in conjunction with the accompanying drawings, wherein:

FIG. 1 is a top plan showing an embodiment of the disclosure illustrating a sample holder having a securing or spring biasing article urging a holding article in contact with a sample having a sample surface, a light detector having a light detector securing or spring biasing article and light sources proximal the sample surface with the light sources positioned in relation to the light sensor generally orthogonal to the sample surface, An optional filter may be positioned between the light source and the sample or between the sample and a spectrometer(s), The light sources may be controlled by the CPU. The output from the light sensor becomes the input to a light detector such as a CCD array within a spectrometer.

FIG. 1A is a side elevation section of FIG. 1.

FIG. 1B is a side elevation section of FIG. 1 with no sample additionally showing a light source securing article.

FIG. 2 is a top plan depicting at least one light source, with a single light source shown in this illustration, with optional filter and with at least one light detector, with a plurality of light detectors illustrated, proximal to the sample surface. This depiction demonstrates an orientation of light detectors relative to the direction of light cast on the sample surface with one light detector onrented at approximately 45 degrees to the direction of the light cast by the light source and a second light detector oriented at approximately 180 degrees from the direction of the light cast by the light source.

FIG. 2A is a section elevation view of FIG. 2 with the sample removed.

FIG. 2B is a top plan depicting a single light source, with optional filter(s) and with multiple light detectors proximal and directed to illuminate the sample surface with both light detectors oriented at approximately 45 degrees to the direction of the light cast by the light source.

FIG. 2C is an elevation view of FIG. 2B.

FIG. 3A is a section from FIG. 3. The light source and light detector may be as described for FIG. 1. Alternative light source may be provided by a plurality of light sources, which may be sequentially fired light emitting diodes emitting discrete wavelengths; where LEDs are employed, the light sensor or light detector may be a broadband photodiode detector central to concentrically positioned LEDs. FIG. 3A illustrates light sources or lamps (and alternatively LEDs) concentrically positioned around a broadband light detector (and alternatively a broadband photodiode detector 255, such light sources as well as the light sources 120/LEDs 257, can be placed in other arrangements. These and other configurations also apply in the use of filtered photodetectors 255 and broadband lamp 123 design.

FIG. 3B is a section from FIG. 3 showing an embodiment where light detectors or light detection fibers surround a least one light source or light source fibers. The light source and light detector may be as described for FIG. 1. In this representation, the centrally positioned light source may be a lamp or light transmitted from a spectrometer; the light detection may be by fiber optics transmission with discrete bandwidth filters between the fiber optics fiber and the sample limiting the transmission by any single or group of fibers.

FIG. 5B is an illustration of the embodiment of FIG. 5 where the sampling head 260 is in the form of a clamp 263. The light detector 80 is depicted as a fiber optic fiber transmitting spectrum from the sample to an array of filtered 130 photodetectors 255 or a spectrometer 170. The output 82 will be managed as shown in FIG. 1D or 1E.

FIG. 5C is a section from FIG. 5B of the array of filtered 130 photodetectors 255. A positioning structure 79 secures and positions the light detector 80 relative to the filtered 130 photodetectors 255.

FIG. 5D is an illustration of the embodiment of FIG. 5 where in at least one clamp jaw 266 structure at least one arc photodetector array 90.

FIG. 5E is a section of the photodetector 255 array of FIG. 5D.

FIG. 6 is a top plan depicting an additional embodiment of the disclosure in a hand held case. The operation of this embodiment is seen in FIG. 1F wherein all components are encased within the case 250.

FIG. 6A is a section elevation of FIG. 6 depicting the sampling head showing the ambient shield, light emitting diodes and photodetector or light detector fixed by affixing articles within the sampling head. The output from the light detector is depicted as well as is the case.

FIG. 6B is an elevation representative of an additional embodiment of the disclosure of this invention and of the embodiment of FIG. 6.

FIG. 6C is a plan view of the embodiment of FIG. 6B illustrating a plurality of light detectors, illustrated here as fiber optic light detectors. Shown in this illustration are two light detectors with one proximal the light source and another distal from the light source.

FIG. 6D is a section detail view from FIG. 6B illustrating the light source, lamp, light source securing article, case, sampling head, light detectors positioned proximal and distal from the light source, light source input and light detector outputs.

FIG. 7 is a side elevation showing another embodiment in a packing/sorting line form of the disclosure. The light source and light detector are positioned proximal the sample.

FIG. 7A is a section elevation of FIG. 7 depicting the light source, and sample conveyance system, bracket fixture, light source securing article, lamp input and spectrometer as a sample moves into illumination from the light source and toward the light detector.

FIG. 7B is a section elevation of FIG. 7 depicting the light detector, and sample conveyance system, bracket fixture, light detector fixture, light detector output, spectrometer, and detector as a sample moves toward and under the light detector.

FIG. 8 is a side elevation showing an additional embodiment of the apparatus disclosed in FIG. 7.

FIG. 8A is a section elevation of FIG. 8 depicting the light shield and at least one curtain, light source, and sample conveyance system as a sample moves into contact with and under the light shield.

FIG. 8B is a section elevation of FIG. 8 depicting the light shield, at least one curtain, light detector and sample conveyance system as a sample moves into contact with and under the light shield.

DETAILED DESCRIPTION

Figure 1C:
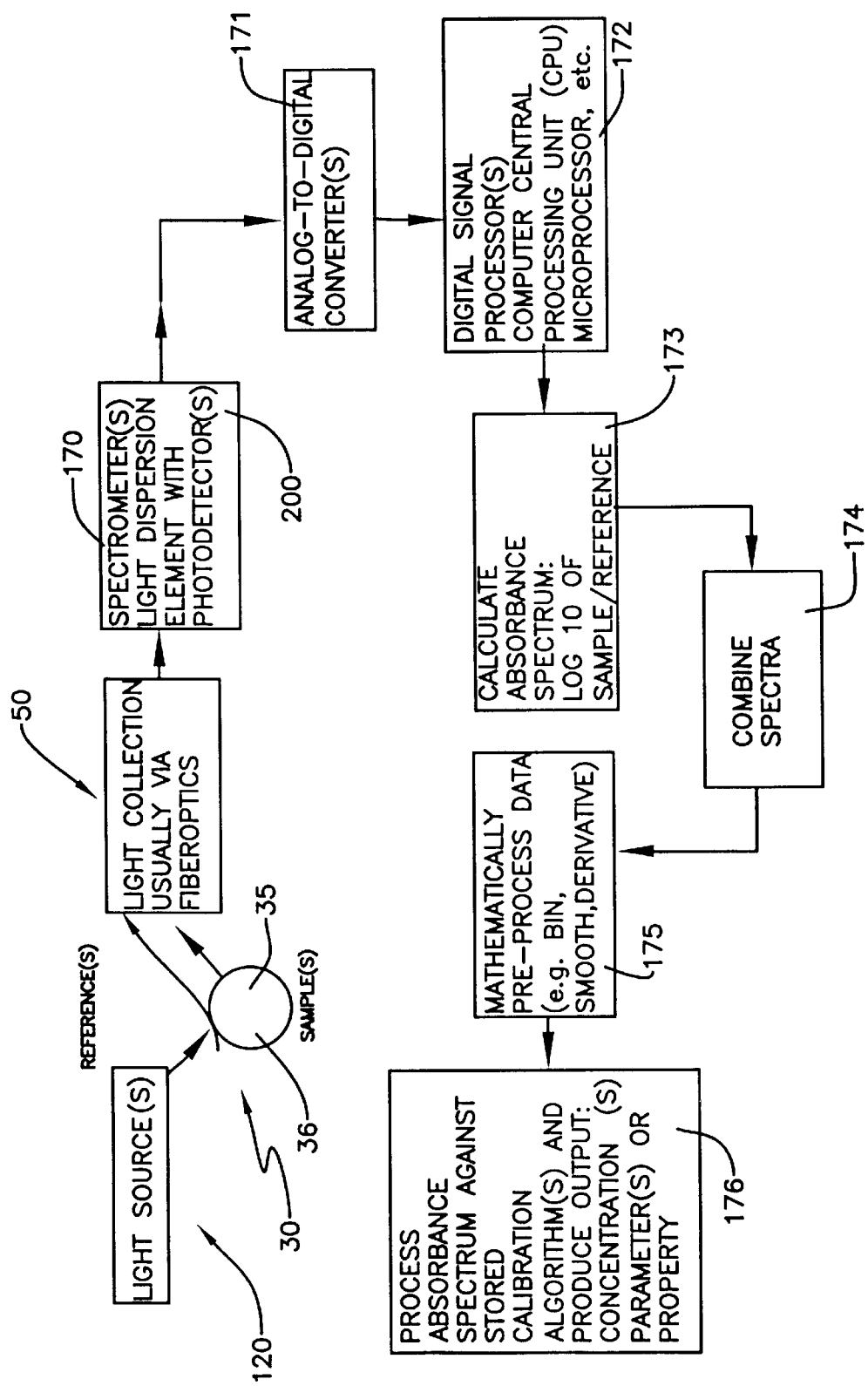
FIG. 1C is a flow diagram demonstrating the method of this invention. The flow diagram is schematically representative of all embodiments of this disclosure.

The apparatus and method disclosed herein is illustrated in FIGS. 1 through 8. FIGS. 1C, 1D, 1E and 1F are flow diagrams demonstrating the method of this invention. The flow diagram FIG. 1C is representative of all embodiments of this disclosure. The flow diagram FIG. 1D illustrates one or more light sources 120 and multiple channels from light detector 50 through final prediction of sample characteristic. FIG. 1D demonstrates the method and apparatus of this disclosure illustrating the light source(s) 120, which may be lamps 123 or other light sources, which illuminate a sample 30 interior 36, light collection channels 1 . . . n, composed for example of fiber optic fibers 80 or photodetectors 255, e.g., light detector 1 . . . n, of the spectra from a sample 30 delivered as input 82 to a spectra measuring device, shown here as spectrometer(s) 1 . . . n. 170. In the preferred embodiment a light source 120 with lamp 123 is external to the spectrometer and is controlled by a CPU 172 which triggers power 125 to the light source 120 lamp 123. Spectrometer 1 . . . n 170 channels output 1 . . . n are converted from analog to digital by A/D converters 1 . . . n 171 and become, for each channel, input to a CPU 172. The CPU 172 is computer program controlled with each step, following the CPU 172 in this flow diagram is representative of a computer program controlled activity. A CPU 172 output is provided for each channel 1 . . . n where the steps of 1) calculation of absorbance spectra 173 occurs for each channel 1 . . . n, 2) combine absorbance spectra 174 into a single spectrum encompassing the entire wavelength range detected from the sample by spectrometers 1 . . . n 170, 3) mathematical preprocessing or preprocess 175, e.g., smoothing or box car smooth or calculate derivatives, precedes 4) the prediction or predict 176, for each channel, comparing the preprocessed combined spectra 175 with the stored calibration spectrum or calibration algorithm(s) 177 for each characteristic 1 . . . x 178, e.g., brix, firmness, acidity, density, pH, color and external and internal defects and disorders, for which the sample is examined, followed by 5) decisions or further combinations and comparisons of the results of quantification of each characteristic, 1 . . . x, e.g., determination of internal and or external defects of disorders 179, 180; determination of color 181; determination of indexes such as eating quality index 182, appearance quality index 183 and concluding with sorting or other decisions 184. Sorting or other decisions 184 may for example be input process controllers to control packing/sorting lines or may determine the time to harvest, time to remove from cold storage, and time to ship. The apparatuses depicted in FIG. 1 through 8 do not all illustrate the entire flow diagram sequence from illumination of sample 30 through determination of the predicted result as is depicted in FIGS. 1C, 1D, 1E and 1F. For signal processing illustrations, reference is made to the indicated drawings.

Absorbance is calculated as follows: once the dark spectrum, reference spectrum and sample spectrum are collected, they are processed to compute the absorbance spectrum, which Beer's law indicates is proportional to concentration. The dark spectrum, which may include background/ambient light, is subtracted from both the sample spectrum and the reference spectrum. The log base 10 of the reference spectrum divided by the sample spectrum is then calculated. This is the absorbance spectrum. It is noted that dark and reference can be collected periodically, i.e., they do not necessarily need to be collected along with every sample spectrum. A stored dark and reference can be used if light source and detector are stable and don't drift. Pre-processing uses techniques known to those practiced in the art such as binning, smoothing, wavelength ratioing, taking derivatives, spectral normalizing, wavelength subtracting, etc. Then the processed absorbance spectrum will be compared with a stored calibration algorithm to produce an output representative or predictive of one or more characteristics, e.g., firmness, Brix, pH, acidity, density, color, and internal and external defects or acidity, of the sample 30.

Figure 1D:
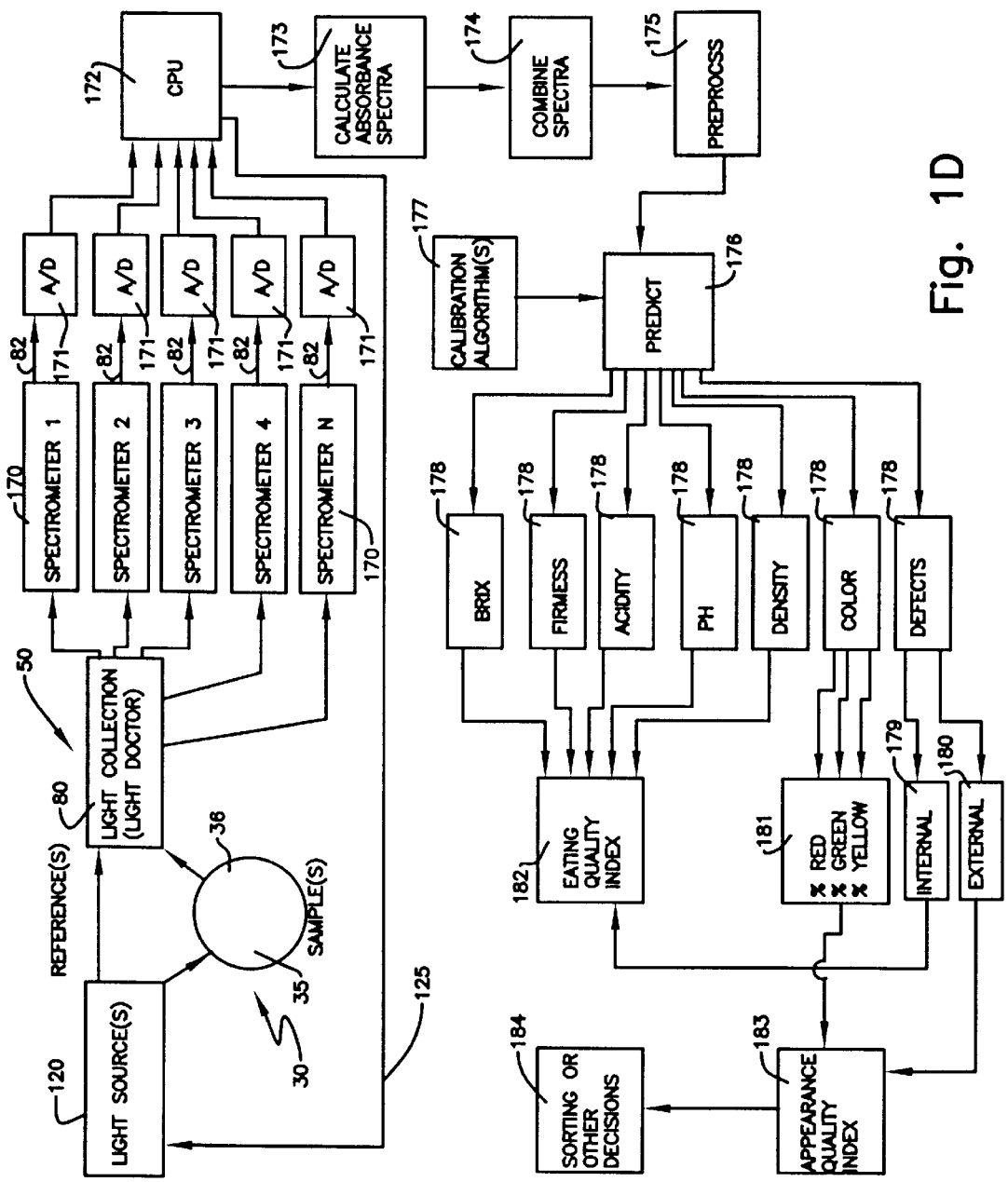
FIG. 1D is a flow diagram demonstrating the method and apparatus illustrating the light source(s) which illuminate a sample, light collection channels 1 . . . n (light detector 1 . . . n) of the spectra from a sample delivered as input to a spectra measuring device, shown here as spectrometer 1 . . . n. Spectrometer 1 . . . n channels output 1 . . . n are converted from analog to digital and become, for each channel, input to a CPU. The CPU is computer program, controlled. The CPU output is also for each channel 1 . . . n.
Figure 1E:
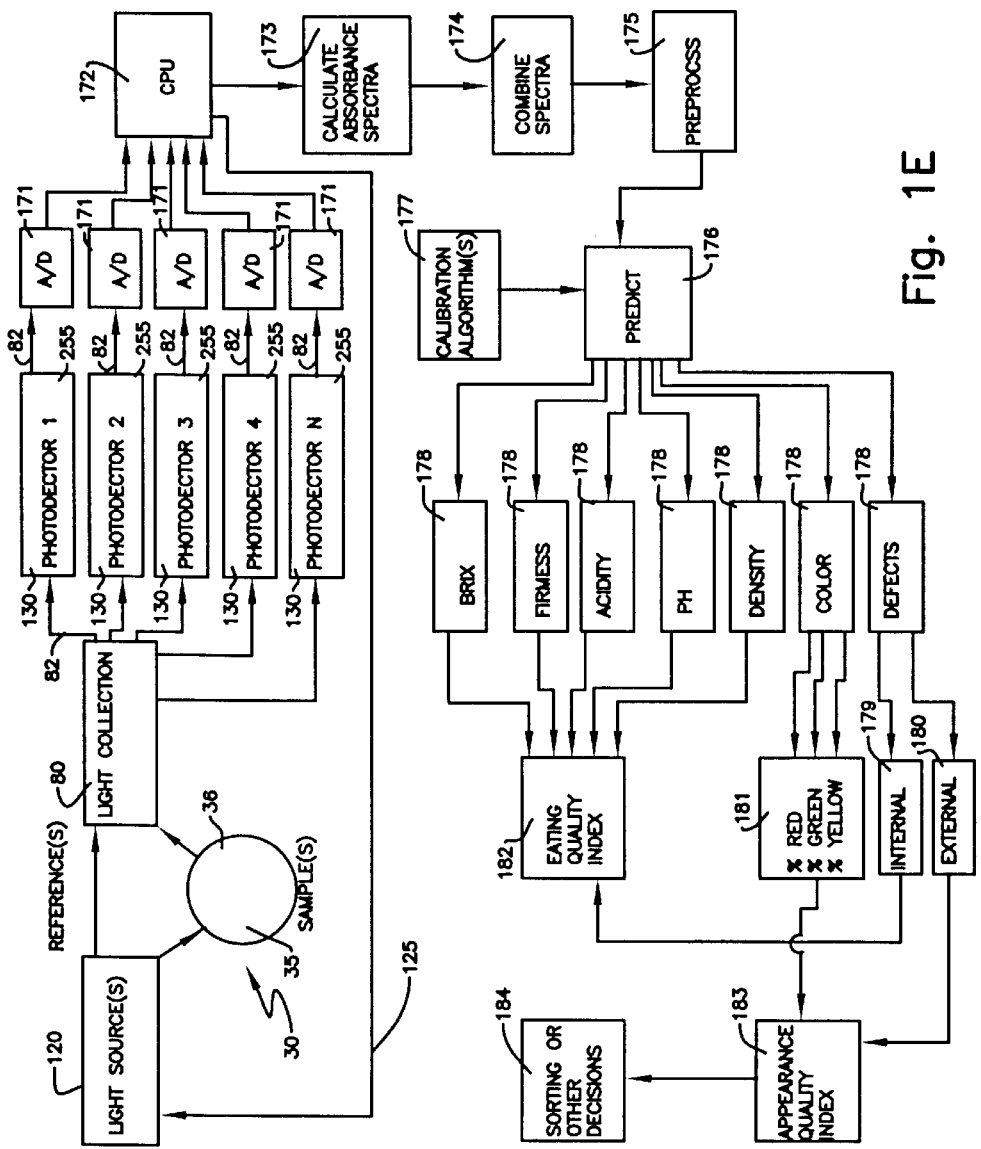
FIG. 1E is a flow diagram demonstrating the method and apparatus illustrating the light source(s) 120 as a broad band source which illuminates a sample 30; at least one discrete wavelength filtered (bandpass) photodetectors 255 having filters 130 for light collection channels 1 . . . n from a sample 30. In this embodiment a light source 120 with lamp 123 is controlled by a CPU 172. The spectrum detected from the sample surface 35 may be communicated by fiber optic fibers as light detectors 80 to the photodetectors 255.

FIG. 1E is a flow diagram demonstrating the method and apparatus illustrating the light source(s) 120 as a broad band source, such as a tungsten halogen lamp, which illuminates a sample 30; at least one, but in an embodiment a plurality, of discrete wavelength filtered (bandpass) photodetectors 255 having filters 130 provide spectrum detection for light collection channels 1 . . . n (photodetector 1 . . . n) of the spectra from a sample 30. In this embodiment a light source 120 with lamp 123 is controlled by a CPU 172 which triggers power 125 to the light source 120 lamp 123. The spectrum detected from the sample surface 35 may be communicated by fiber optic fibers as light detectors 80 to the photodetectors 255. The management of the detected spectra is as described for FIG. 1D. An alternative to this embodiment may use an AOTF, (acousto-optic tunable filter) to replace the at least one or a plurality of photodetectors 255 as the spectrum detection device.

Figure 1F:
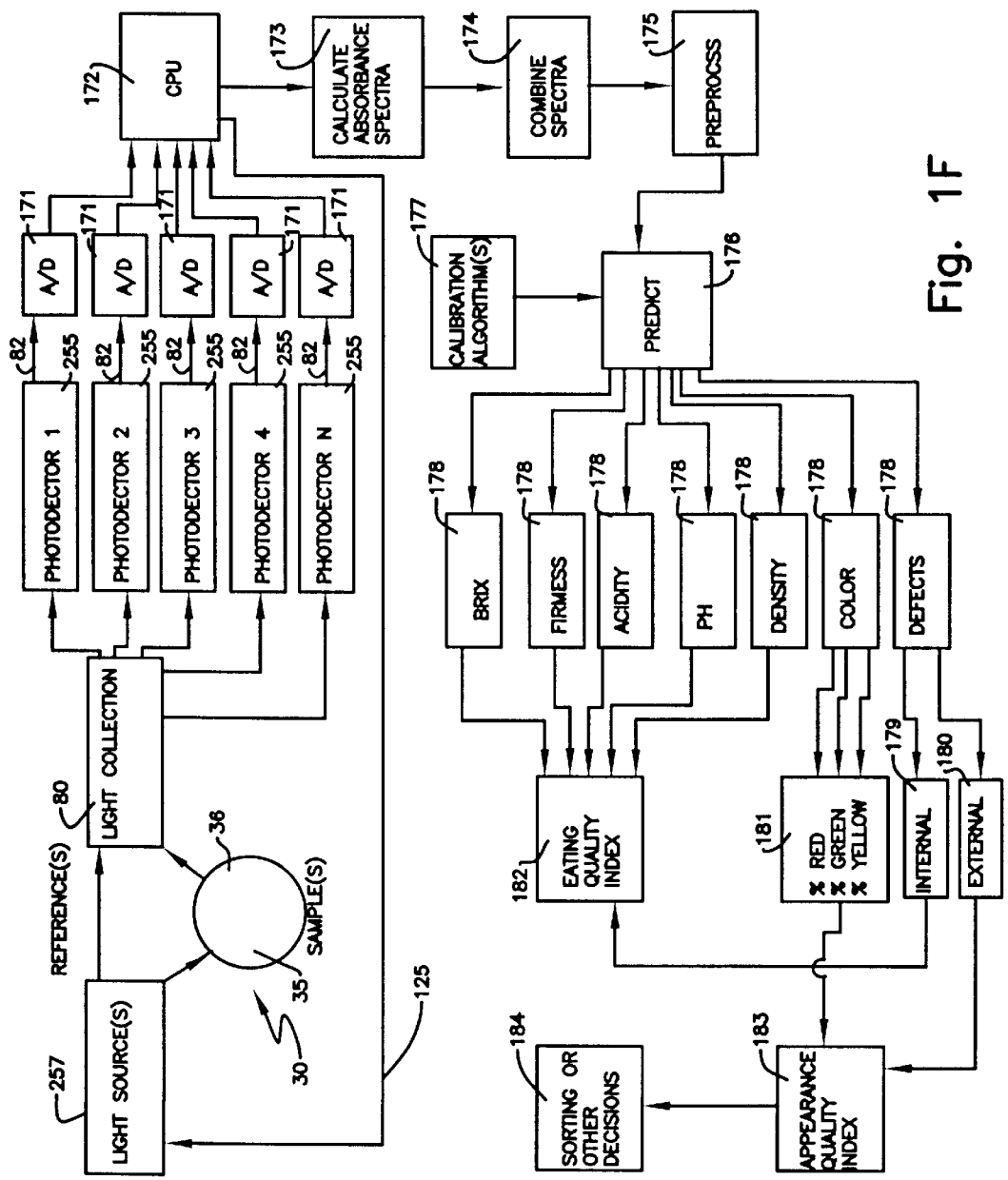
FIG. 1F is a flow diagram demonstrating the method and apparatus illustrating the light source(s) provided by at least one discrete wavelength light emitting diodes 257 to illuminate a sample 30; at least one broadband photodetector 255 and at least one broadband photodetector 255 for each LED 257 for light collection channels 1 . . . n (photodetector 1 . . . n) of the spectra from a sample.

FIG. 1F is a flow diagram demonstrating the method and apparatus illustrating the light source(s) provided by at least one, but in an embodiment a plurality of discrete wavelength light emitting diodes 257, which may be sequentially fired or lighted by a CPU trigger for power 125 to illuminate a sample 30; at least one broadband photodetector 255 and, in an alternative embodiment a least one broadband photodetector 255 for each LED 257, provide spectrum detection for light collection channels 1 . . . n (photodetector 1 . . . n) of the spectra from a sample. The management of the detected spectra is as described for FIG. 1D. Alternative light sources for this embodiment include but are not limited to tunable diode lasers, laser diode and a filter wheel placed between the light source(s) and sample or between the sample and photodetector(s).

FIGS. 1, 1A and 1B depict an embodiment of a Nondestructive Fruit Maturity and Quality Tester 1 for measuring and correlating characteristics of fruit with combined Visible and Near Infra-Red Spectrum showing an embodiment of the disclosure illustrating a sample holder 5 having a securing or spring biasing article 9 urging a holding article 12 against and in contact with a sample 30. The holding article depicted in FIG. 1 is illustrated as essentially a hemisphere sized to receive a sample 30. The sample has a sample surface 35. At least one light source 120 will be employed proximal the sample surface 35. The light source 120 is comprised of at least one lamp 123, optional filters 130. Here illustrated are two light sources 120 each directed essentially orthogonally to the sample surface 35 and illuminating the sample 30 approximately 60 TO 90 degrees relative to each other. A light detector 80 is depicted as directed to detect light from the sample surface 35 at approximately 30 TO 45 degrees relative to the direction of the light cast from either light source 120. The light detector 80 is illustrated as positioned by a light detector fixture 50 having a light detector securing or spring biasing article 60 placing, holding and or urging a light detector 80 into contact with the sample surface 35. Monitoring of the light source 120 is depicted by light detectors 80 depicted as directed toward the lamp 123 output; the output 82 of these reference light detectors 80 is detected by a reference spectrometer 170; an alternative to the use of two spectrometers 170 will be the sequential measurement of reference light detectors 80 and the light detector 80 directed to the sample surface 35. All light detector 80 are fixed by light detector fixtures 50 by light detector securing or spring biasing articles 60 to a plate 7 or other containing device such as a case. The securing article 9 urging the holding article 12 against the sample 30 also urges the sample against the light detector 80. The securing article 9 and holding article 12 in combination with the light detector 80 and light detector securing article 60 secure and prevent the sample 30 from movement. The sample 30 is shown, in FIG. 1, as an apple. The light sources 120 may be, for example, tungsten/halogen lamps. An optional filter 130 or filters 130 functioning as heat block, bandpass and or cutoff filters, separately or in combination, may be positioned between the lamp 123 and the sample 30 or between the sample 30 and the light detector 80. The light sources 120 may be lamps 123, provided for example by external 50 Watt, 75 Watt, or 150 Watt lamp sources controlled by a CPU 172. Power 125 can be provided by power supply from a spectrometer 170 or from an alternate power supply. Both the light source(s) and the spectrometer(s) are controlled by a CPU 172 and their operation can be precisely controlled and optimally synchronized using digital input/ output (I/O) trigger. The light detector 80, shown here as a fiber-optic sensor, provides a light detector output 82 which becomes the input to a spectrometer 170, or other spectrum measuring or processing instrument, which is detected by a detector 200, e.g., at least one light detection device or article, such as a CCD array which may be a CCD array within a spectrometer 170. The sample holder 5, light detector fixture 50 and light detector securing article 60 and light sources 120 with light source securing article 122 are affixed to a plate 7, for experimental purposes but will be otherwise enclosed and or affixed in a container, case, cabinet or other or other fixture for commercial purposes, e.g., applications include and are not limited to sample measurements on high speed sorting and packing lines, harvesters, trucks, conveyor-belts and experimental and laboratory. Other brackets, fixtures or articles may be employed to secure or position either sample holders 5, light detectors 50 and or samples 30 requiring only that the device or method used retain the sample 30 in position relative to the light source 120 and light detector 50 during the period of measurement; fixing methods including welds, bolts, screws, glue, sheet metal forming and other methods may be used to secure such items for either experimental or commercial purposes.

FIGS. 2, 2A, 2B, 2C, 2D and 2E depicts an alternative embodiment of the Nondestructive Fruit Maturity and Quality Tester 1 depicting a single light source 120, with lamp 123 and optional filter 130 and with multiple light detectors 80 in contact with the sample surface 35. This depiction of the relative positioning of the light detectors 80 with the sample 30 or sample surface 35 is directed to the shielding of the light detector 80 from ambient light and is intended to demonstrate either direct contact between the light detector 80 and the sample surface 35 or shielded a shield 84 composed, for example, by bellows, a foam structure or other pliable or compressible article or apparatus providing a sealing structure or shield method of insuring that the light detector 80 is shielded from ambient light and light from the light source 120 and receives light spectrum input solely from the sample 30. The positioning of the light source 120 relative to the light detectors 80 illustrate a positioning of one light detector 80 at angle theta of approximately 45 degrees to the direction of the light as directed by the light source 120 to illuminate the sample 30. The second light detector 80, in this illustration, is at angle gamma of approximately 180 degrees to the direction of the light as directed by the light source 120. The positioning of the light detector 80 at approximately 180 degrees to the direction of the light as directed by the light source 120 may be a position utilized for the detection of internal disorders within the sample, e.g., internal disorders within Tasmania Jonagold apples, such as water core, core rot, internal browning/breakdown, carbon dioxide damage, and, in some cases, insect damage/infestation. The light detectors 80 in this illustration are suggestive of the many light detector 80 positions possible with the positioning dependent on the sample and the characteristic or characteristics to be measured or predicted. In this illustration the light detectors 80 are positioned to detect within the same plane as the light directed from the light source 120. The orientation of 180 degrees between light source 120 and light detector 80 will be preferred for smaller samples. Larger samples 30 will attenuate light transmission thus requiring the location of the light detector 80 proximal the light source 120 to insure exposure to light spectrum output 82 characteristic of the sample 30. The orientation of the light source 120 and light detectors 80 is sensitive to fruit size, fruit skin and fruit pulp or flesh properties. The orientation where the sample 30 is an apple will likely preclude a 180 degree orientation because of limitations in proximity and intensity of the light source 120 as being likely to damage or burn the apple skin. However, orange skins are less sensitive and may withstand, without commercial degradation, a light source 120 of high intensity and closely positioned to the orange surface. Generally, the signal output or light detector output 82 is dependent on the orientation of the light source 120 relative to the sample 30 and sample surface 35 and the light detector 80.

The light detector outputs are illustrated as providing inputs to spectrometers. The outputs may be combined to provide a single input to a single spectrum measuring and detecting instrument or may separately form inputs to separate spectrometers. For the case of a single measuring instrument, light shutters may be used and alternately activated to provide light input from each measuring location separately in series, thus producing two spectra from different depths or locations of a sample.

Figure 2E:
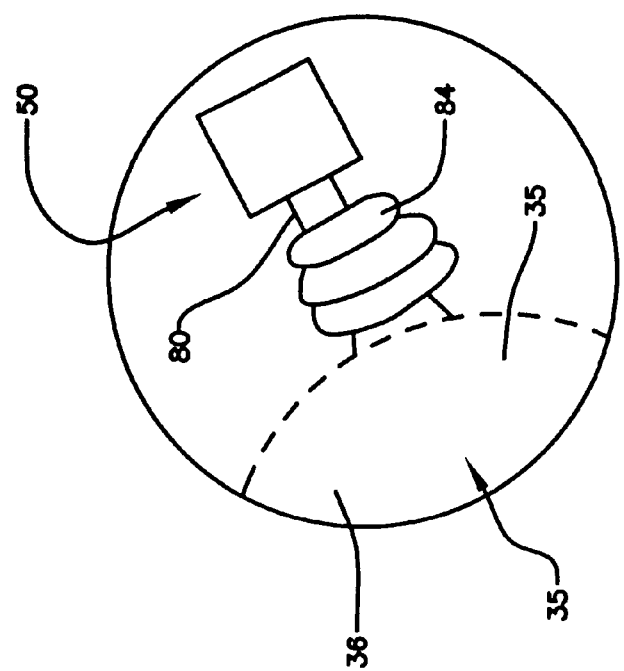
FIG. 2E is a detail of a shielding device between the light detector of FIG. 2 and a sample. Shown in this illustration is a shield in the form of a bellows. Other shielding apparatus and methods will provide like shielding structure.
Figure 2D:
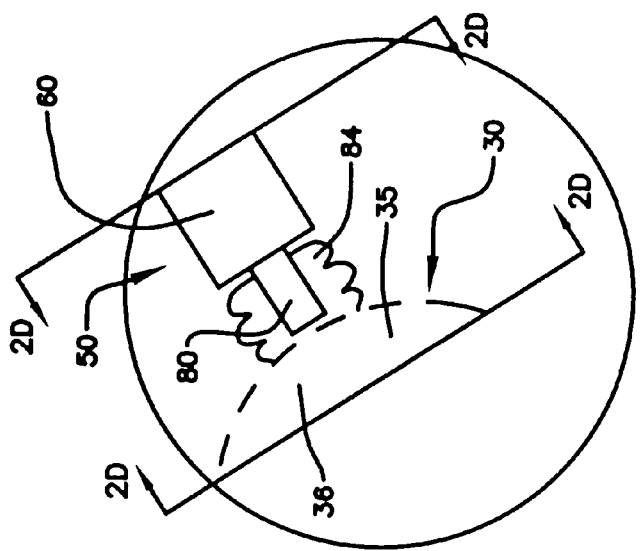
FIG. 2D is a section from FIG. 2C depicting a shielding method or apparatus, e.g., in the form of a bellows or other shielding article shielding the light detector from ambient light and directing the light detector to detect light spectrum output from the sample.

FIGS. 2B and 2C depict an alternative orientation of light detectors 80 where the light detectors 80 are oriented at angle theta of approximately 45 degrees to the direction of the light as directed by the light source 120. This illustration demonstrates two light detectors 80 positioned approximately 90 degrees apart and positioned to detect light from approximately the same plane. One of ordinary skill in the art will recognize from these illustrations that the positioning of the light source or light sources and light detector or detectors will depend on the measurement intended. FIGS. 2D and 2E depict a shielding method or apparatus, e.g., in the form of a bellows or other shield 84 article shielding the light detector from ambient light and enabling the light detector to solely detect light spectrum output from the sample. The shield 84 structure may be formed of a flexible or pliant rubber, foam or plastic which will conform to the surface irregularities of the sample and will provide a sealing function between the shielding material and sample surface which will eliminate introduction of ambient light into contact with the light detector. The shield 84 is depicted in the form of a bellows in FIGS. 2D and 2E.

FIGS. 1, 2–4, 6, 7 and 8 depict light sources which may be provided by spectrometers 170 (as in the case of FIG. 3) or external lamps controlled by CPU 172 (as in case of FIGS. 1, 2, 4–8). In all cases of FIGS. 1–4, 6, 7, and 8, tungsten halogen lamps or the equivalent are used which generally produce a spectrum within the range of 250–1150 nm when the filament temperature is operated at 2500 to 3500 degrees kelvin. The light source, for the invention disclosed herein may be a broadband lamp, which for example, but without limitation, may be a tungsten halogen lamp or the equivalent, which may produce a spectrum within the range of 250–1150 nm; other broadband spectrum lamps may be employed depending upon the sample 30, characteristics to be predicted, and embodiment utilized The light detector 80 output 82 in these embodiments will generally be received by a spectrometer 170 having a detector 200 such as a CCD array.

Figure 3:
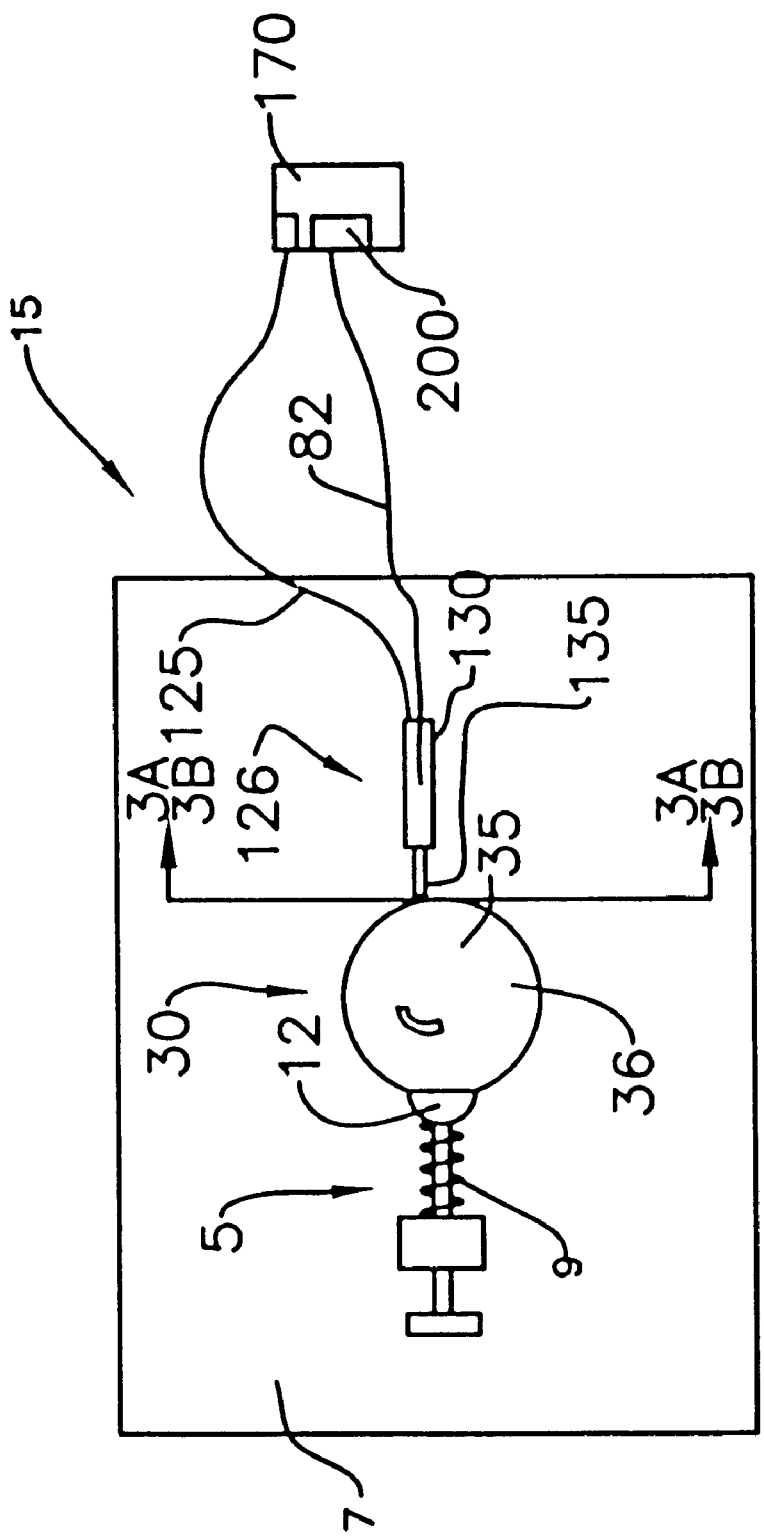
FIG. 3 is a top plan depicting an alternative embodiment of a light source and light detector configuration where the light source is communicated by fiber optics.
Figure 5:
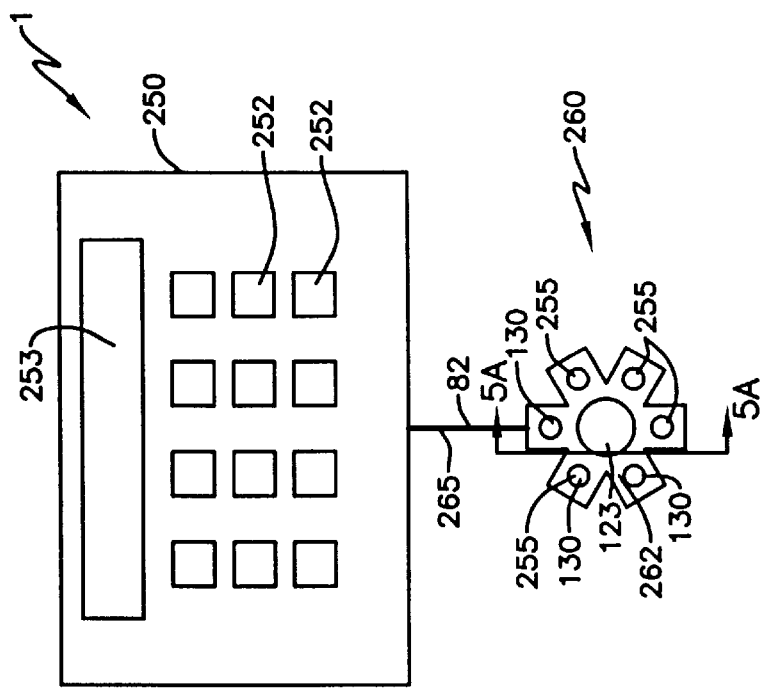
FIG. 5 is a top plan depicting an alternative embodiment of the disclosure in a hand held case showing a light source and light detector configured in a sampling head. In this embodiment at the sampling head at least one light source, which may be a tungsten halogen lamp, is positioned in relation to discrete-wavelength filtered photodetectors. A shield is illustrated as an ambient shield. The operation of this embodiment is seen in FIG. 1E wherein all components are encased within the case 250.

FIGS. 3, 3A and 3B depict an alternative embodiment of a Nondestructive Fruit Maturity and Quality Tester-Combined Unit 15 of a combined unit 126 having a combined source/detector 135. The source of light and method of light detection in this embodiment may be a light source 120, lamp 123 and light detector 80 configuration where the light source 123 lamp 123 is communicated by fiber optics from an illumination source, e.g., a lamp such as the lamp at a spectrometer 170; light detection is provided by light detectors 80, e.g., fiber optics or other manner of light transmission, positioned in varying relationships to the lamp 123 as shown in FIGS. 3A and 3B. FIG. 3A is a section from FIG. 3 showing the combined unit 126 where a combined source/detector 135 has an alternative source of light and light detection; the source of light, depicted as a plurality of sources, may be sequentially fired light emitting diodes 257 emitting discrete wavelengths; the light detection may be a broadband photodiode detector 255 central to concentrically positioned LEDs. The combined unit 126 and sample holder 5 are mounted to a plate 7 or other mounting or containing fixture, case, cabinet or other device suitable for commercial or experimental purposes, for example with a bracket or other mounting article, so as to be fixed or as to have a spring or other biasing function to urge the combined unit 126 and sample holder 5 against the sample. A light shield 84, as depicted in FIGS. 2D and 2E may be used between the combined source/detector 135 and the sample surface 35. FIG. 3B is a section from FIG. 3 showing an additional embodiment of a combined unit 126 where a centrally positioned light source 120 lamp 123, for example light via fiber optics from a tungsten halogen lamp, is concentric to at least one and, as depicted here a plurality, of discrete wavelength photodetectors. The output of the at least one detection fibers or light detectors 80 is the input to a spectrometer 170 or other spectral measuring instrument such as a photodetector 255. Depicted is a spectrometer 170 having a detector 200. Alternatively, light source delivery and detection for the embodiment of FIG. 3B may be by a bifurcated reflectance probe; alternatively, it is recognized that a reflectance probe may provide one or more light delivery sources and one or more light detectors providing inputs to one or more spectrometer. While FIG. 3A illustrates LEDs 257 concentrically positioned around a broadband photodiode detector 255, it will be recognized that the LEDs of this embodiment, as well as the light sources 120 of other embodiments, can be placed in other arrangements, e.g., the photodiode detector 255, as well as the detectors 80 of other embodiments, can be 180 degrees opposite a circle of LEDs 257 and the sample 30 placed between the LEDs 257 and the photodiode detector 255, e.g., for cherries or grapes; alternatively, the LEDs 257 can be placed on an arc, equidistant and 180 degrees opposite from the photodetector 255 in relationship to the sample 30. These two arrangements are suggestive of the positioning relationships of LEDs 257 (light sources 120), photodiode detectors 255 (light detectors 80) and samples 30 as well as the instance where other types of light source and detectors are employed including, for example, the use of filtered photodetectors 255 with a broadband lamp 123, as illustrated in FIG. 5. In each embodiment the particular sample 30 type combined with the particular characteristics to be predicted will dictate the pattern of light source 120 and light detector 80 in relation to the sample 30. Additionally, it is to be recognized that light source used herein includes broadband lamps such as the tungsten halogen lamp, LEDs and other light emitting devices; light detectors used herein includes fiber optic fibers, photodiode detectors and other devices sensitive to and capable of detecting light.

Figure 4:
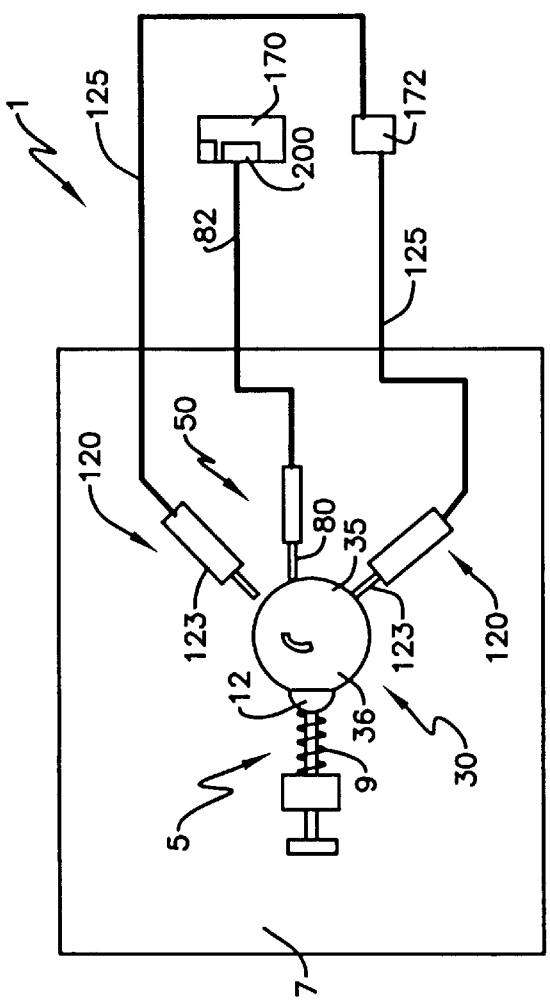
FIG. 4 is a top plan depicting an alternative embodiment of a light source and light detector configuration.

FIG. 4 is a top plan depicting an alternative embodiment of a Nondestructive Fruit Maturity and Quality Tester 1 showing at least one light source 120 and lamp 123 and light detector 50 configuration where at least one, and as depicted in this illustration two, light source 120 and lamps 123 are communicated by fiber optics to or proximal the sample surface 35, from an illumination source, e.g., a lamp 123 or other external light source. Light detection is provided by light detectors 80, e.g., fiber optics or other method of light transmission. In this embodiment the light sources 120 and light detector 80 are in contact with the sample surface 35. The light detector 80 detects the light spectrum output from the sample 30 and providing light detector input 82 to a spectrum measuring or processing instrument or method including, for example, a spectrometer 170 having a detector 200. For certain samples, the light detector 80 will be inserted into the sample 30 thus effecting a shielding of the light detector 80 from ambient light, e.g., on harvester-mounted applications or in a processing plant where the product will be processed such as sugar beets or grapes. Otherwise, the light shield 84 depicted in FIGS. 2D and 2E is applicable to the interrelationship of the sample 30 and sample surface 35 with the light detector 80 and light source 120 and lamp 123. Illustrated in FIG. 4 is the connection of the light detector outputs 82 from the at least one light detector 80 forming the input to a spectrum measuring or processing instrument. It will be recognized that each component of this embodiment will be affixed by conventional methods to a plate 7 or other mounting or containing fixture, case, cabinet or other device suitable for commercial or experimental purposes.

FIG. 5 is a top plan depicting an alternative embodiment of the Nondestructive Fruit Maturity and Quality Tester 1 in a hand held case 250 showing a light source 120 and at least one light detector 80, shown here as six light detectors 80, configuration in the form of a sampling head 260. In this embodiment at the sampling head 260 at least one light source 120 lamp 123 is positioned in relation to light detectors 80 provided by at least one discrete-wavelength photodetector 255. Shown in FIG. 5 are a plurality of discrete-wavelength photodetectors 255, filling the combined function of light detector 80, and spectrum detecting instrument such as a CCD array detector 200. The operation of this embodiment is seen in FIG. 1E wherein all components are encased within the case 250. Electronic and computer communication between the sampling head 260 and the computer control circuitry is via electronic signal cabling 265 or wireless including infrared or other such transmission method or apparatus. The sampling head 260 ambient shield 262 will provide a shielding method or apparatus, e.g., fulfilling the same or similar structural function as the shield 84 in FIGS. 2D and 2E, in shielding the at least one photodetector 255 and lamp 123 from ambient light. The sampling head 260 and ambient shield 262, depicted in FIGS. 5 and 5A may be formed from a pliable polyfoam within which the at least one lamp 123 and at least one photodetector 255 may be secured by a fixture article. The material or structure forming the sampling head 260 and ambient shield 262 may be flexible or pliable foam, in the form of a bellows or other shielding article similar to that depicted in FIGS. 2D and 2E. The use of a pliable polyfoam to form the ambient shield 262 will serve to seal out or preclude exposure, by a sealing action between a sample surface 35 and the ambient shield 262, of the at least one photodetector 255 and lamp 123 from ambient light. Other shielding apparatus and methods will provide adequate shielding structure including bellows, a case or box enclosing the sampling head 260 and sample 30 or other such article providing shielding structure between ambient light and the interface between the sampling head 260, the at least one photodetector 255 and lamp 123 and the sample 30 and sample surface 35. The operation of this embodiment is seen in FIG. 1E wherein all components are encased within the case 250.

In this illustration, FIG. 5, the sampling head is arranged so that the photodetectors are concentrically arrayed in relation to the light source. The light source may be communicated by fiber optics from an illumination source, e.g., a lamp within the case or by placement of a lamp within the sampling head, e.g., the broadband output lamp, e.g., tungsten halogen, is physically located centrally to concentrically arrayed photodetectors. The light source may be present to be in contact with the sample surface or proximal to the sample surface. Electrical communication is effected between the light source and photodetectors and a computer processor.

Figure 5A:
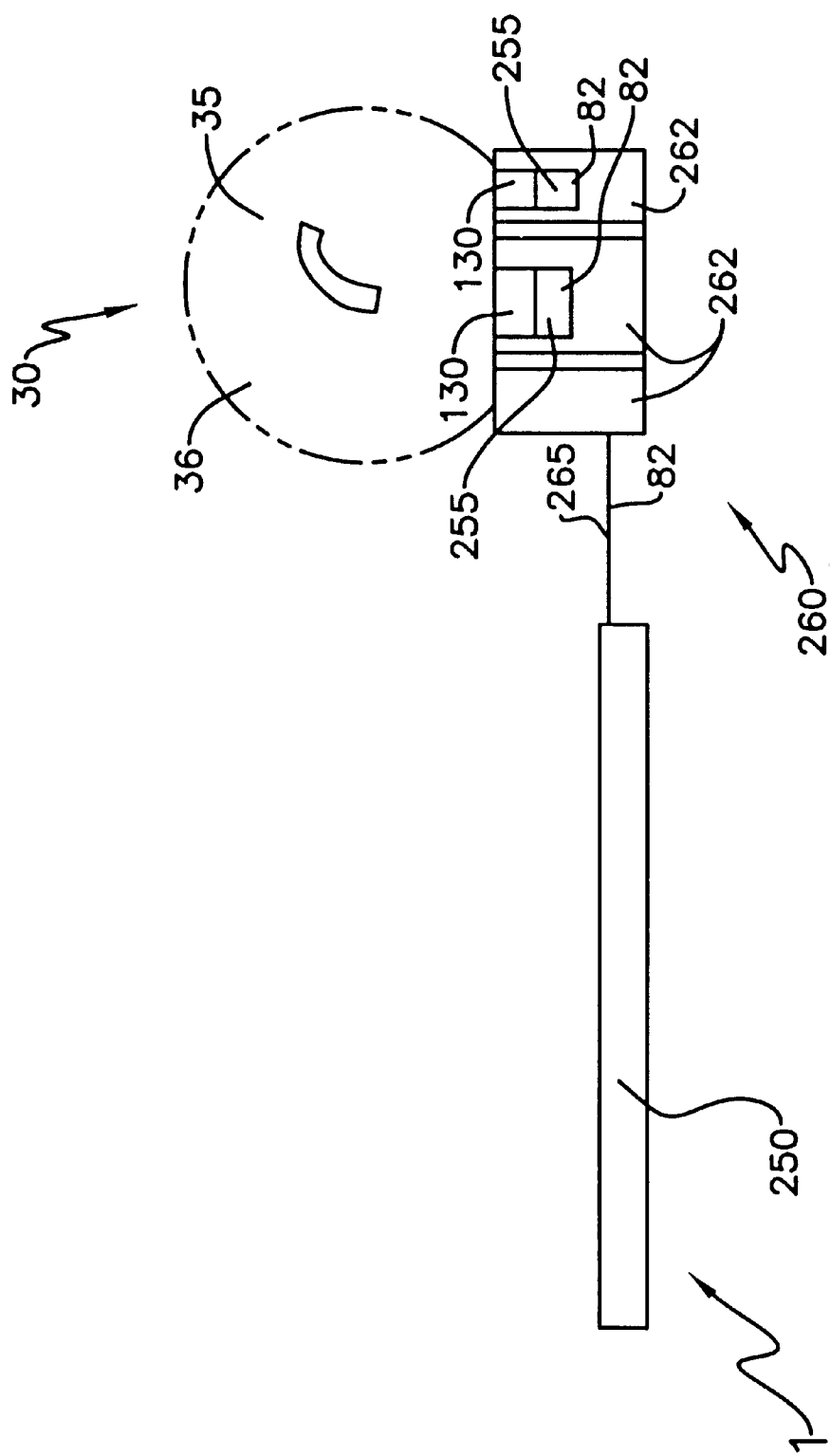
FIG. 5A is a side elevation of FIG. 5 depicting a sample positioned on the sampling head.

FIGS. 5 and 5A illustrate the sampling head 260 arranged so that at least one, and as illustrated in FIG. 5, a plurality of discrete-wavelength filtered 130 photodetectors 255 are concentrically arrayed in relation to the centrally positioned at least one light source 120. The light source 120 lamp 123 which may be communicated by fiber optics from an illumination source, e.g., a lamp within the case 250 or may, for particular samples 30, e.g., oranges, be present to be in contact with or closely proximal the sample surface 35. Electrical communication and light communication is effected between the light source 120 and photodetectors 255 and a spectrometer 170 by fiber optics and or wiring, printed circuit paths, cables. The photodetectors 255 fulfill a spectrometer or spectral measurement function, provides the input 82 which will be processed with microprocessor stored calibration algorithm to produce an output representing one or more parameters of the sample. FIG. 5A is a side elevation of FIG. 5 depicting a sample positioned on the sampling head.

FIGS. 5B, 5C, 5D and 5E illustrate embodiment of the invention directed particularly to small samples 30, e.g., grapes and cherries, where the sampling head 260 is in the form of a clamp 263 having at least two clamp jaws 266 which receive and secure within at least one jaw 266 structure at least one lamp 123 having a light source input 125 and in at least one clamp jaw 266 structure at least one light detector 80 such that the jaws 266, when the clamp 263 is closed, receive a sample 30 positioned to have the at least one lamp 123 and the at least one light detector 80 proximal the sample surface 35. The light detector 80 is depicted as a fiber optic fiber transmitting spectrum from the sample to an array of filtered 130 photodetectors 255 or a spectrometer 170. The output 82 will be managed as shown in FIG. 1D or 1E. FIG. 5B depicts a light detector 80 as a fiber transmitting spectrum from a sample 30 to be displayed on a filtered 130 photodetector array 255 where the fiber 80 is contained and positioned to transmit the detected spectrum from the sample 30 so that the fiber 80 is central to a concentrically arrayed filtered 130 photodetectors 255. A positioning structure 79, which may be tubes interconnected to position the fiber light detector 80 central to the photodetector array 255, secures and positions the light detector 80 relative to the filtered 130 photodetectors 255. A collimating lens 78 will be positioned between the light detector 80 fiber and the array 255 to insure that light from the light detector 80 is normal to the filtered 130 photodetector array 255. FIG. 5F depicts an arc photodetector array 90 received and secured within at least one jaw 266 structure where the photodetectors 255 within the photodetector array 90 are preferably equidistant from the light source 120 or lamp 123.

FIG. 5D is an illustration of the embodiment of FIG. 5 where the sampling head 260 is in the form of a clamp 263 having at least two clamp jaws 266 which receive and secure within at least one jaw 266 structure at least one lamp 123 and in at least one clamp jaw 266 structure at least one arc photodetector array 90 such that the jaws 266, when the clamp 263 is closed, receive a sample 30 positioned to have the at least one lamp 123 and the at least one arc photodetector array 90 proximal the sample surface 35. The arc photodetector array 90 is depicted as an array of filtered 130 photodetectors 255 which will preferably be equidistant from the lamp 123 when a sample 30 is received. The output 82 will be managed as shown in FIG. 1D or 1E.

Figure 6F:
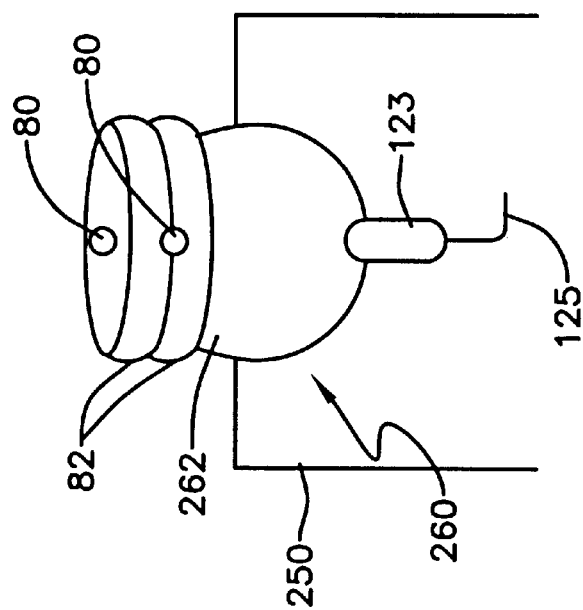
FIG. 6F is a section detail from FIG. 6E showing light detectors affixed within the sampling head ambient shield positioned proximal and distal from the light source, a lamp with lamp input, light detector outputs and a case.

FIGS. 6 through 6F illustrate an additional embodiment of the Nondestructive Fruit Maturity and Quality Tester 1. FIG. 6 is a top plan depicting an additional embodiment of the disclosure in a hand held case 250 form showing a light source 120 in the form of LEDs 257 and light detector 80, in the form of a photodetector 255, configuration in the form of a sampling head 260. With the LED 257 and photodetector 255 configuration, the photodetector 255 is used without filters, i.e., wavelength bandpass filters, and is sensitive from ~250–1150 nm. Alternative devices or methods for providing light source and light detection includes, but is not limited to diodelasers and other light sources producing a discrete wavelength spectrum. In this embodiment at the sampling head 260 at least one LED 257, and as illustrated in FIG. 6, a plurality of LEDs 257, is positioned in relation at least one photodetector 255. A method or article is required to shield the LEDs 257 and photodetector/photodiode detector 255 from ambient light which is illustrated as an ambient shield 262 including structures of compressible and pliable foam, bellows as indicated by the shield 84 structure of FIGS. 2D and 2E and other such materials, structures or articles. In this illustration the sampling head 260 is arranged so that the at least one photodetector/photodiode detector 255 is central to concentrically arrayed discrete wavelength LEDs 257. In this embodiment the light emitting diodes 257 fulfill the function of light source and are sequentially fired or lighted with the spectrum output detected by the at least one photodetector/photodiode detector 255. The photodetector 255 output 82 is processed as demonstrated in FIG. 1F.

The photodetector 255 is responsive to a broad range of wavelengths, both visible and near-infrared (i.e., ~250–1150 nm). When each LED 257 is fired, the light enters the sample 30, interacts with the sample 30, and re-emerges to be detected by the photodetector 255. The photodetector 255 produces a current proportional to the intensity of light detected. The current is converted to a voltage, which is then digitized using an analog-to-digital converter. The digital signal is then stored by an embedded microcontroller/microprocessor. The microcontroller/microprocessor used in the preferred embodiment is an Intel 8051. However, other microprocessors and other devices and circuits will perform the needed tasks. The signal detected by the photodetector 255 as each LED 257 is fired is digitized, A/D converted and stored. After each LED 257 has been fired and the converted signal stored, the microprocessor stored readings are combined to create a spectrum consisting of as many data points as there are LEDs 257. This spectrum is then used by the embedded microprocessor in combination with a previously stored calibration algorithm to predict the sample properties of interest. Signal processing then proceeds as shown in FIG. 1F. FIG. 6A is a section elevation of FIG. 6 depicting the sampling head 260 showing the ambient shield 262, composed for example of compressible foam or bellows or other such structure, e.g., a rubber plunger, originally designed for a vacuum pick-up tool which looks much like a toilet plunger, but has a more gentle curve and is available in a variety of sizes including 1 mm diameter and larger; in certain of these embodiments a 20 mm rubber plunger was used with a pickup fiber optic operating as the "handle" that couples to the plunger. The sample then makes a seal with the plunger prior to measurement. Other devices or methods will also provide the requisite sealing structure, as described in this specification. Also shown are light emitting diodes 257 and light detector/photodiode detector 80 fixed by affixing articles within the sampling head 260. The affixing articles will be composed of bracket articles and other mounting structure recognized by one of ordinary skill. The output 82 from the light detector 80 is depicted as well as the case 250 with processing as shown in FIG. 1F.

FIGS. 6B, 6C and 6D are representative of an additional embodiment of the disclosure of this invention where a sampling head 260 is affixed in a case 250, light detectors 80 are affixed by affixing articles within the sampling head 260. The sampling head 260 receives a sample 30 which is positioned to be illuminated by a light source 120 lamp 123. This embodiment depicts the case 250 as having a cover which serves as an ambient shield 262. Additionally, the structure of the sampling head 260 may be of a compressible or pliable foam or a bellows which may provide the structure allowing an ambient shield 262. Ambient light can also be measured after the sample 30 is in place, but before the light source 120 lamp 123 is turned on. This ambient light signal is then stored and subtracted accordingly for subsequent measurements. A light source input power 125 is depicted for example from a spectrometer 170 or may be from a CPU 172 trigger or other external lamp source and/or power supply. Outputs 82 from the light detector/photodiode detectors 80 are depicted and processed as shown in FIG. 1F.

FIG. 6C is a plan view of the embodiment of FIG. 6B illustrating a pluralilty of light detectors, illustrated here as fiber optic light detectors. Shown in this illustration are two light detectors with one proximal the light source and another distal from the light source with the purpose being to provide two different pathlengths, shallow and deep, by taking the difference between the far or deep spectrum and the near or shallow spectrum data of greater accuracy can be obtained. This difference method provides a pathlength correction to improve concentration or property or sample characteristic predictions.

Figure 6E:
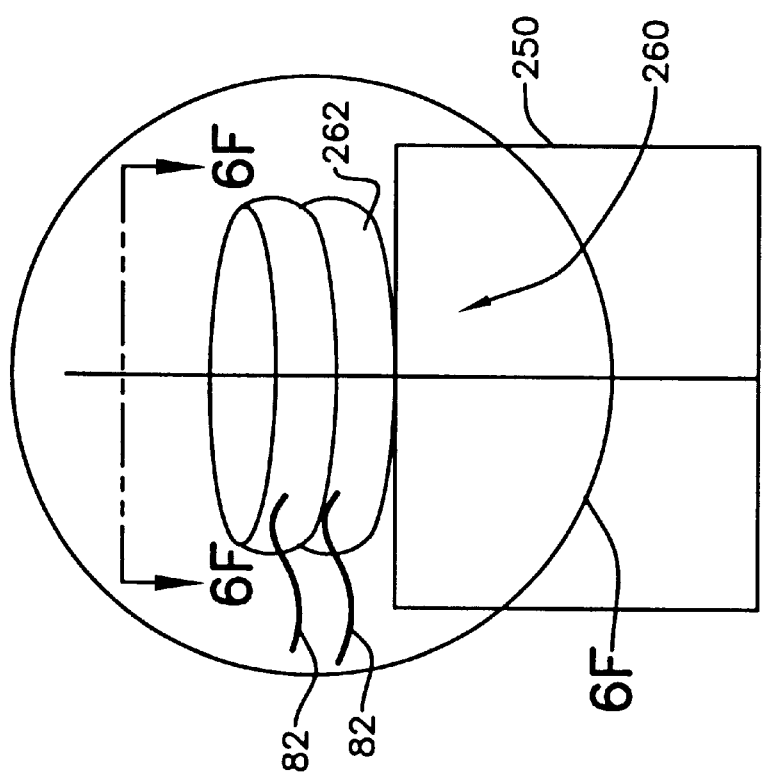
FIG. 6E is an elevation view of an embodiment of the disclosure of FIG. 6 wherein the sampling head structure provided the ambient shield structure.

FIGS. 6E and 6F are representative of an embodiment of the disclosure wherein the lamp 123 is positioned within the sampling head 260. Alternatively, the lamp 123 may be positioned by an affixing article within the ambient shield 262.

Another embodiment in a packing/sorting line form of the disclosure is depicted in FIGS. 7, 7A and 7B illustrating a light source 120 and light detector 80 affixed and positioned by bracket articles 275, light detector fixture 50 and light source securing articles 122 which will be recognized as mounting structure from which at least one light source 120 and at least one light detector 80 will be suspended, rigidly secured and otherwise positioned including the use of such as rods, bars and other such bracket article 275 fixtures. The at least one light source 120 is positioned to illuminate a sample 30, depicted in this drawing as an apple. The at least one light detector 80 is positioned by bracket articles 275 and light detector fixture 50 to detect the light spectrum output from the illuminated sample 30. Samples 30, in this illustration are conveyed by a sample conveyor 295. Total exposure to the at least one light source 120 and at least one light detector 80 will be determined by the intensity of the light source used and the nature of the sample being interrogated. For apples, exposure times of 5–10 msec or less are commonly used to provide multiple measurements per apple at line speeds up to 20 fruit/second. The at least one light detector 80 depicted in FIG. 7 illustrates a separation of the light detector 80 from the light source 120 of approximately 90 degrees with both light detector 80 and light source 120 essentially orthogonal to the sample in the same plane. However, for each embodiment of this disclosure, the positioning of the light detector(s) 80 and of the light sources(es) 120 relative to each other and relative to the sample is dependent on the characteristics of the sample and of the qualities sought to be measured. For example, the light source 120 may be positioned to be directed essentially orthogonal to the sample surface 30 in a plane oriented 90 degrees from the plane to which the light detector 80 is directed. The light source 120 and light detector 80 are positioned proximal the sample 30. The light source 120 lamp 123 may be powered from a spectrometer 170 or other external source, as noted in the discussion of FIG. 1. The light detector 80 may be a single fiber optic fiber with the light spectrum detected forming the output 82 to a spectrum detection instrument such as a spectrometer 170 and detector 200. The processing of the light spectrum detected is as described and set out in FIG. 1C.

Figure 7C:
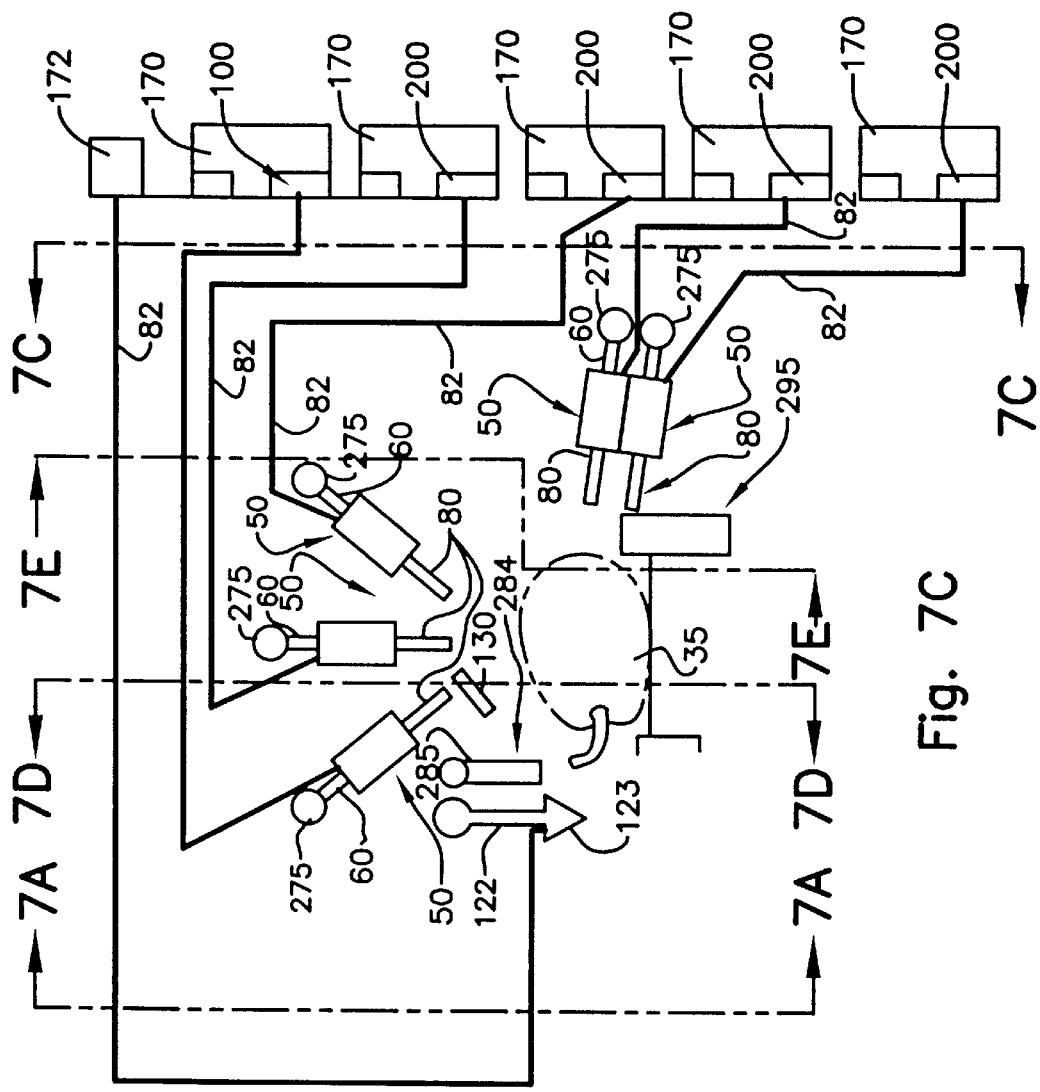
FIG. 7C is an elevation depicting at least one light detector 80 and as shown a plurality of light detectors 80 representative of measurements of a plurality of spectrum regions.
Figure 7E:
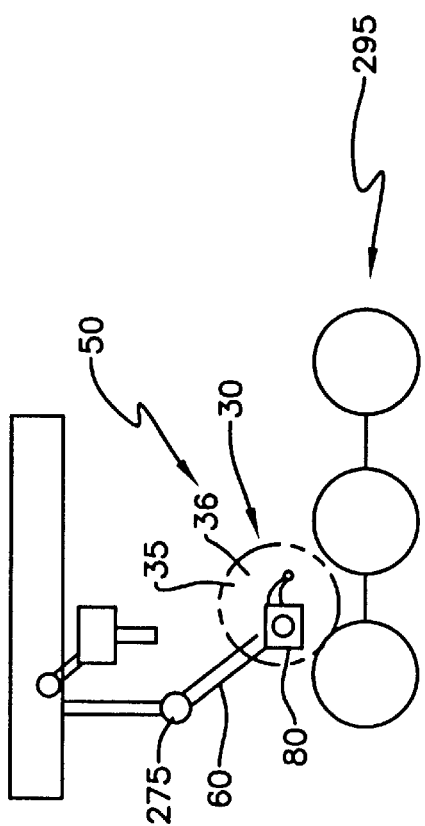
FIG. 7E is a section from FIG. 7C showing one of the reference light detectors 80.
Figure 7D:
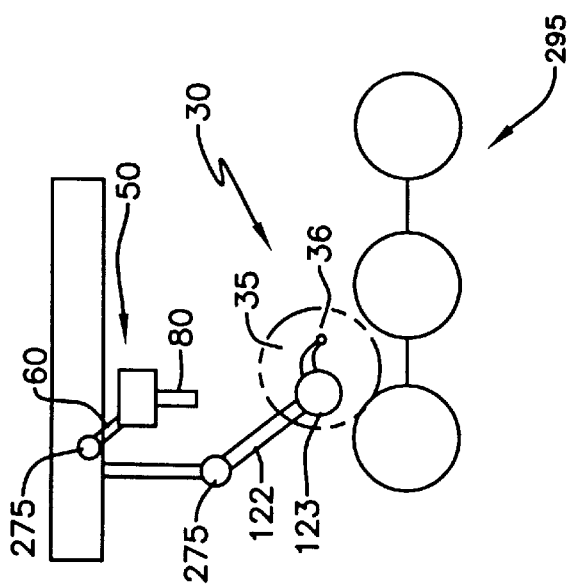
FIG. 7D is a section from FIG. 7C showing the lamp 123 oriented to illuminate the sample from the side. As illustrated, the sample as an apple is illuminated from the stem side.

Another embodiment directed to sorting/packing lines is seen in FIGS. 7C, 7D and 7E depicting at least one light detector 80 and as shown a plurality of light detectors 80 representative of measurements of a plurality of spectrum regions. A filtered 130 light detector 80 is representative of the detection of spectrum of 700 to 925 nm, another light detector 80 is representative of detection of red pigments and chlorophyl in the 500 to 699 nm range and water, alcohols and physical quality (e.g., firmness, density) information available in the 926 to 1150 nm range, another light detector 80 is representative of detection of the yellow pigment region in the range of 250 to 499 nm. Two additional light detectors 80 are shown positioned opposite a light source 120 lamp 123 such that the sample will pass between the lamp 123 and light detector 80 and is representative of an input to two reference spectrometers 170, one monitoring the 250–499 nm wavelength region and the other monitoring the 500–1150 nm region. Where the sample is an apple it will be expected that the reference channel additionally will not detect spectrum out of the sample and will indicated the presence or absence of a sample. The output of the reference channel(s) can be used as an object locator to determine which spectra from the sample light detector(s) to retain for use in prediction. Shielding may be utilized between the light source 120 lamp 123 and the light detectors 80 and or sample 30, e.g., options include but are not limited to 1) a light shield 284 as a curtain 285 may extend from a bracket fixture 275 between the light source 120 lamp 123 and light detectors 80 reducing the direct exposure of the light detectors 80 to the light source 120 lamp 123, 2) the light shield 285 may extend between the light source 120 lamp 123 and light detectors 80 and sample 30 wherein an aperture will be formed in the light shield 284 between the light source 120 lamp 123 and sample 30 limiting surface reflection from the sample surface 35 to the light detectors 80 and 3) the light shield 284 may provide filter 130 function, e.g., heat blocking, cutoff and bandpass, between the light source 120 lamp 123 and sample surface 35 limiting the possibility of heat or burn damage to the sample 30.

An additional embodiment is seen in FIGS. 8, 8A and 8B wherein at least one light shield 284 is positioned by a bracket article 275 to separate the at least one light source 120 and lamp 123 from the at least one light detector 80 as a sample 30 is conveyed by a sample conveyor 295 under and past a light source 120 and lamp 123 toward and under a light detector 80. The light shield 284 may be a curtain 285 and is depicted in FIG. 8 as a curtain 285 composed of at least one portions and as shown in FIG. 8A of two portions or a plurality of portions, each suspended from a bracket article 275. Where there are a plurality of curtain 285 portions, the respective curtain 285 portions will overlap and separate as the sample 30 passes.

In this embodiment, as shown in FIG. 8, the sample 30, for example an apple, is conveyed by a packing/sorting conveyance system 295. A cycle will be repeated as each sample 30 moves toward, into contact with, under and past the light shield 284. The packing/sorting conveyance system 295 will have samples 30 sequentially positioned on the conveyance system 295 such that the space between sample 30 is minimal generally in relation to the size of the sample 30. As the sample 30 moves toward, but is not in contact with, the light shield 284 the sample 30 will be illuminated by the light source 120 while the light detector 80 will detect only ambient light and will be shielded from the light source 120. As the sample 30 moves into contact with and under the light shield 284 the sample 30 will, while continuing to be illuminated by the light source 120, be exposed to the light detector 80 which will detect spectrum from the sample 30. When the sample 30 moves past the light shield 284 the light detector 80 will again be shielded from the light source 120 and will detect only ambient light. The light source 120 may, for example, be a tungsten/halogen lamp or light transmitted by optics to illuminate the sample 30. The light detector 80, for example a optic fiber detector, is positioned such that the sample surface 35 will be proximal to the light detector 80 as the sample 30 contacts and passes under the light shield 284. The light shield 284 may be composed of a flexible or pliable sheet opaque to the spectra to which the light detector 80 is sensitive and may be comprised, for example, of silicone rubber, Mylar, thermoplastics and other materials. The light detector 80, light shield 284 and light source 120 will be mechanically affixed by bracket articles 275 or other mounting apparatus or methods readily recognized by those of ordinary skill in the art or measurement at packing/sorting systems.

An alternative configuration of the embodiments of FIGS. 7 and 8 will employ a plurality of light sources 120 including, for example a light source 120 illuminating the sample 30 from the top with a second light source 120 illuminating the sample 30 from the side or two light sources 120 illuminating the sample 30 from opposite sides illustrating the multiple positions which may be employed for light sources 120. A plurality of light detectors 80 will view the same or different sample surface 35 locations with each light detector 80 output 82 either sensed by a separate spectrometer or combined to form a single output 82. Where a plurality of outputs 82 are received by a plurality of spectrometers 170 at least one spectrometer 170 will have a neutral density filter installed to block some percentage, e.g. 50%, of the output 82 from the light detector 80 with this spectrometer 170 to provide data from a particular spectral range, e.g., approximately 700 to approximately 925 nm. A second spectrometer will not use a filter and will saturate from approximately 700 to 925 nm but will yield good signal to noise (S/N) data from approximately 500 to 699 nm and approximately 926 to 1150 nm. Other outputs 82 to filtered input spectrometers 170 will permit the examination of specific spectral ranges. Additionally, this method allows the use of the same exposure times on both, or a plurality of, spectrometers 170 making them easier to control in parallel. This is essentially the dual exposure approach using filtered input 82 to the spectrometer 170 rather than different exposure times. The blocking of light to one spectrometer 170 effects the same result as using a shorter exposure time. The dual intensity approach proves problematic because the high and low intensity spectra are not easily pasted or combined together due to slope differences in the spectra, however the dual intensity approach may be preferred for predicting certain parameters (e.g., firmness, density) with certain sample types (e.g. stored fruit or oranges). While the dual exposure approach yields excellent combined spectra, both approaches provide useable combined spectra, which are necessary for firmness and other parameter prediction and also improved Brix accuracy.

Typically, Partial Least Squares (PLS) regression analysis is used during calibration to generate a regression vector that relates the VIS and NIR spectra to brix, firmness, acidity, density, pH, color and external and internal defects and disorders. This stored regression vector is referred to as a prediction or calibration algorithm. Spectral pre-processing routines are performed on the data prior to regression analysis to improve signal-to-noise (S/N), remove spectral effects that are unrelated to the parameter of interest, e.g., baseline offsets and slope changes, and "normalize" the data by attempting to mathematically correct for pathlength and scattering errors. A pre-processing routine typically includes "binning", e.g., averaging 5–10 detector channels to improve S/N, boxcar or gaussian smoothing (to improve S/N) and computation of a derivative. The 2nd derivative is most often used, however, the 1st derivative can also be used and the use of the 4th derivative is also a possibility. For firmness prediction, data is often used after binning, smoothing and a baseline correction or normalization; where no derivative is used. For Brix and other chemical properties, a 2nd-derivative transformation often is best.

Using a Principal Components Analysis (PCA) classification algorithm, soft fruit and very firm fruit can be uniquely identified from moderately firm fruit. Also, under-ripe and ripe fruit can be separated and spoiled, e.g., higher pH, or rotten fruit can be identified for segregation. The NIR spectra of whole apples, and other fruit, in the approximately 250–1150 nm region also show correlation with pH and total acidity. The 250–699 nm wavelength region contains color information, e.g., xanthophylis, yellow pigments, absorb in the 250–499 nm region; anthocyanin, which is a red pigment, has an absorption band spanning the 500–550 nm region, improves classification or predictive performance, particularly for firmness. An example is the prediction of how red a cherry is by measuring and applying or comparing the anthocyanin absorption at or near 520 nm to the pertinent predictive or classification algorithm. Under-ripe oranges, having a green color, can be predicted by measurement of sample spectrum output 82 in the chlorophyll absorption region (green pigments) at or near 680 nm and applying the measured output 82 spectrum to the pertinent predictive algorithm. The spectrum output from the sample, in the 950–1150 nm region has additional information about water, alcohols and acids, and protein content. For example, sample water content relates to firmness in most fruit with water loss occurring during storage. High pH fruit, often indicative of spoilage, can also be uniquely identified in the presence of other apples using a classification algorithm.

The present disclosure is a non-destructive method and apparatus for measuring the spectrum of scattered and absorbed light, particularly within the NIR range of 250–1150 nm, for the purpose of predicting, by use of the applicable predictive algorithm, particular fruit characteristics including sugar content, firmness, density, pH, total acidity, color and internal and external defects. These fruit characteristics are key parameters for determining maturity, e.g., when to pick, when to ship, when and how to store, and quality, e.g., sweetness/sourness ratio and firmness or crispness for many fruits and vegetables. These characteristics are also indicators of consumer taste preferences, expected shelf life, economic value and other characteristics. Internal disorders can also be detected, e.g., for Tasmania Jonagold apples, including disorders such as water core, core rot, internal browning/breakdown, carbon dioxide damage, and, in some cases, insect damage/infestation. The disclosure simultaneously utilizes 1): the visible absorption region (about 250–699 nm) that contains information about pigments and chlorophyll, 2) the wavelength portion of the short-wavelength NIR that has the greatest penetration depth in biological tissue, especially the tissue of fruits and vegetables (700–925 nm), and 3) the region from 926–1150 nm, which contains information about moisture content and other O—H components such as alcohols and organic acids such as malic, citric, and tartaric acid.

Benchtop, handheld, portable and automated packing/sorting embodiments are disclosed. The benchtop embodiment will generally be distinguished from the high speed packing/sorting embodiment through the greater ease of examining the sample 30 with more than one intensity light source 120, i.e., lamps 123 or light sources 120 controlled with more than one voltage or power level or more than one exposure time. A benchtop embodiment discussed herein utilizes a dual intensity light source 120, e.g., by utilizing dual voltages or dual exposure times or other methods of varying the intensity of the light source 120 used to illuminate the sample 30. Alternatively, the light detector 80 may be operated to provide at least one exposure at one lamp 123 intensity and, for example, the light detector 80 may provide dual or a plurality of exposures at 1 lamp intensity. The method of providing dual or a plurality of exposures at one lamp intensity is accomplished as follows: the light detector 80 exposure time is adjustable through basic computer software control. In the computer program, two spectrum of different exposure times are collected for each sample 30. The benchtop method may, as preferred by the operator, involve direct physical contact between the sample surface 35 and the apparatus delivering the light source 120, e.g., at least one light detector 80 may penetrate the sample surface 35 into the sample interior. A high speed packing/sorting embodiment generally will be limited in the delivery or the exposure of the light source 120, relative to or at the sample surface 35, resulting from the limited time, usually a few milliseconds, the sample 30 will be in range of the light source 120. Multiple passes or arrangements of multiple light sources 120 and multiple light detectors 80, including photodetectors 255 and other light detection devices, will permit, in the highspeed packing/sorting embodiment, the exposure of the sample to multiple light source 120 intensities. The handheld embodiment generally will allow sampling of a limited number of items by orchard operators, i.e., in inspection of fruit samples on the plant or tree, and from produce delivered for packing/sorting, to centralized grocery distribution centers or individual grocery stores.

Obtaining data over the wavelength region of 250–1150 nm is only possible using a multi intensity or multi exposure measurement, i.e., dual intensity or dual exposure as in the preferred embodiment. While one spectrometer can be used to cover the 500–1150 nm region, a second spectrometer is necessary to cover the 250–499 nm region. The number of different light source intensity or exposures required is dependent on the characteristics of the sample and of the detector 200. The spectrum acquired at longer detector 200 exposure times or higher light source intensity saturates the detector pixels, for some detectors, e.g., Sony ILX 511, or Toshiba 1201, from ~700–925 nm, yet yields excellent S/N data from ~500–699 nm and from ~926–1150 nm. The low intensity or shorter exposure time spectrum is optimized to provide good S/N data from 700–925 nm. Accurate firmness predictions of fresh and stored fruit requires the 700–925 nm region and the 500–699 nm, e.g., pigment and chlorophyll, plus the 926–1150 nm region. Addition of the 250–499 nm region, e.g., yellow pigments known as xanthophylls which absorb light, will improve prediction of firmness and other parameters such as Brix, acidity, pH, color and internal and external defects. There is high correlation between the spectrum output from the sample 30 in the 926–1150 nm region with water content. Stored fruit appears to have higher relative water content than fresh fruit and less light scattering. The chlorophyll and pigment of a sample 30 is predicted by correlation with the sample spectrum output 82 in the 250–699 nm region, with this correlation likely being the most important for prediction of firmness of fresh fruit, while the longer wavelength water region may be more important for accurate firmness measurement of stored fruit.

Just as in the longer NIR wavelength regions, the 700–925 nm region also contains absorption bands from carbon-hydrogen, oxygen-hydrogen, and nitrogen-hydrogen bonds, e.g., (CH, OH, NH). In the case where protein is key component of interest, the 926–1150 nm region is of greatest interest. However, pre-sprout condition in grain, for example, can be predicted by examination of the sample output spectrum in the 500–699 nm region.

The preferred embodiment of the apparatus is composed of at least one light source 120, a sample holder 5 including, for example a sorting/packing sample conveyor 295 and other devices and methods of positioning a sample 30, with at least one light detector 80, i.e. optical fiber light sensors in the preferred embodiment, detecting the sample spectrum output 82 to be received by a spectrum measuring instrument such as a spectrometer 170 with a detector 200, e.g., a CCD array, with the signal thus detected to be computer processed, by a CPU 172 having memory, and compared with a stored calibration algorithm, i.e., stored in CPU 172 memory, producing a prediction of one or more characteristics of the sample. The at least one light source 120 and at least one light detector 80 are positioned relative to the sample surface 35 to permit detection of scattered and absorbed spectrum issuing from the sample. Bracket fixtures 275, brackets and other recognized positioning and affixing devices and methods will be employed to position light sources 120, light detectors 80 and sample holders 5. In the preferred embodiment the positioning of the light source 120 and light sensor or light detector 80 will be such as to shield 84 the light detector 80 from direct exposure to the light source 120 and will limit the light detector 80 to detection or exposure of light transmitted from the light source 120 through the sample 30. The light source 120 may be fixed in a conical or other cup or shielding container which will allow direct exposure of the light source 120 to the sample surface while shielding the light source 120 from the light detector 80. Alternatively, the light detector 80 may be fixed in a shielding container, e.g., a shield 84 or ambient shield 262, thus shielding the light detector 80 from the light source 80 and exposing the light detector 80 solely to the light spectrum transmitted through the sample 30 from the light source 80 to the light detector 80. The spectrum detected by the light detectors 80, i.e., the signal output 82, is directed, as input, to at least one spectrometer 170 or other device sensitive to and having the capability of receiving and measuring light spectrum. In the preferred embodiment two or more spectrometers 170 are employed. One spectrometer 170 monitors the sample channel, i.e., the light detector 80 output 82, and another spectrometer 170 monitors the reference, i.e., light source 120 channel. If the lamp 123 is turned on and off between measurements, ambient light correction can be done for both light detector 80 and light source 120 channel, e.g., spectrum collected with no light is subtracted from spectrum collected when lights are on and stabilized. Alternatively, the light source 120 can be left on and ambient light can be physically eliminated using a shield 84 or ambient shield 262, such as a lid or cover or appropriate light-tight box. The discussion of shielding of the light detector 80 composed of fiber optic fibers applies as well to photodetectors 255 and the utilization of light sources other than tungsten halogen lamps including for example light emitting diodes 257.

Another alternative with multiple sampling points and thus multiple light detectors 80, as with fiber-optic sensors, is to converge all or some sampling points, as depicted in FIG. 4, back to a single sample or light detector 80 channel spectrometer 170, e.g., using a bifurcated, trifurcated or other multiple fiber-optic spectrometer 170 input. Multiple or a plurality of sample points, i.e., light detectors 80, provides better coverage of a sample 30, e.g., sampling is more representative of the sample 30 as a whole, or allows multiple points, e.g., on a conveyor belt full of product, to be measured by a single spectrometer 170 thus providing an "average" spectrum that is used to predict an average property such as Brix for all sample 30 or light detector 80 channels.

In the preferred embodiment two or more spectrometers 170, or at least two spectrometers 170 are used for reference and or measurement. A spectrometer 170 used in gathering data for this invention utilized gratings blazed at 750nm to provide coverage from 500–1150 nm. Additionally, spectrometers 170 operating in the 250–499 nm wavelength region can be included to provide expanded coverage of the visible region where xanthophylls, e.g., yellow pigments, absorb light. Information in the output 82 spectrum detected from 1000–1100 nm also contains repeated information, if a cutoff or long-pass filter is not used, from 500–550 nm, e.g., regarding Anthocyanin, which is a red pigment, has an absorption band spanning the 500–550 nm region, which improves classification or predictive performance, particularly for firmness.

The spectrometers 170 used in the preferred embodiment have charge-coupled device (CCD) array detectors 200 with 2048 pixels or channels, but other array detectors 200, other light detectors 80, including other detector 200 sizes vis-a-vis array size or other method of detector size characterization, may be used as would be recognized by one of ordinary skill in the art. One of the two spectrometers 170 monitors the light source 120 intensity and wavelength output directly, providing a light source reference signal 81 that corrects for ambient light and lamp, detector, and electronics drift which are largely caused by temperature changes and lamp aging. The other spectrometer(s) 170 receives the light detector 80 signal output 82 from one or more light detectors 80 which are sensing light output from one or more samples 30 and/or one or more locations on a sample 30, e.g., at multiple points over a single sample 30, such as an apple, or at multiple points over a sample conveyor 295 belt of apples, grapes or cherries, or a different sample 30, e.g., a different lane on a packing/sorting line, can be measured with each additional spectrometer 170. Each light sensor, e.g., light detector 80(photodetector 255 or other light sensing apparatus or method), in the preferred embodiment represents a separate sample 30 or different location on the same sample 30 or group of samples 30. Spectra from all spectrometers 170 are acquired, in the preferred embodiment, simultaneously. Depending on the type of spectrometer, A/D conversion can occur in parallel or series for each spectrometer (parallel preferred). The computer then processes the spectra and produces an output. Current single CPU computers process spectra in series. A dual CPU computer, two computers, or digital signal processing (DSP) hardware can perform spectral processing and provide output in parallel.

In an alternative embodiment spectra from the wavelength region from about 250–1150 nm, the near-infrared spectra, is examined from samples 30, e.g., fruit including apples. In this particular experiment, a reflectance fiber-optic probe was used as the light detector 80. While the spectrophotometer 170 used to collect the data, i.e., sense the spectrum output 82 from the light detector 80, was a DSquared Development, LaGrande, Oreg., Model DPA 20, one of ordinary skill in the art will recognize that other spectrometers and spectrophotometers 170 may be used. The spectrophotometer 170 referenced employed a five watt tungsten halogen light source 120, a fiber-optics light sensor to detect the spectrum or output 82 from the sample 30 and provide the light sensor signal input 82 to the spectrometer 170. Other lamps 123 or light sources 120 may be substituted as well as other light sensors or light detectors 80. The light detector signal input 82 to the spectrometer 170, in this embodiment, is detected by a charge coupled device array detector 200. The output from the charge coupled device array detector is processed as described above. Firmness and Brix were measured using the standard destructive procedures of Magness-Taylor firmness ("punch test") and refractometry, respectively. In this embodiment the NIR spectra is detected by an array detector 200 which permits recording or detection of 1024 data points. The 1024 data points are smoothed using a nine-point gaussian smooth, followed by a 2nd-derivative transformation using a "gap" size of nine points. Partial least squares EELS) regression was used to relate the 2nd-derivative NIR spectra to Brix and firmness. To ensure that false correlation was not occurring, the method of leave-one-out cross-validation was used to generate standard errors of prediction. In cross-validation, the prediction model is constructed using all but one sample; the Brix and firmness of the sample left out is then predicted and the process repeated until all samples have been predicted. The validated model can then be used to nondestructively predict Brix and firmness in unknown whole fruit samples. This information guides harvest decisions indicating time to harvest, which fruit is suitable for cold storage, where the fruit is classified from acceptable to unacceptable characteristics of quality or consumer taste, which fruit to be removed from the sorting/packing operation as not meeting required characteristics, e.g., firmness, Brix, color and other characteristics.

This disclosure of embodiments of an apparatus and method is directed to the simultaneous measurement and use of more than one spectral region from a sample. In this embodiment the use of the chlorophyll absorption region and the NIR region, including the highly absorbing 950–1150 O—H region, is accomplished by exposing the sample, e.g. apple, to more than one intensity source of light or by exposing the light detector 80 at more than one exposure time, e.g., a dual intensity source of light or at least two intensities of light, or by detecting light from a sample with more than one light detector 80 such that each light detector 80 is sensitive to a different spectrum, e.g., by filtering one or more light detectors 80 with filtering either between the sample 30 and the light detector 80 or between the light detector 80 output 82 and the spectrometer 170 input. FIG. 1 illustrates filtered light sources 120 allowing exposure of the sample 30 to different light intensities. FIG. 2 illustrated the use of more than one light detector 80 where filtering between the sample 30 and light detector 80 allows detection of different spectral regions. Shown in FIG. 3A, where the light source is a plurality of discrete wavelength LEDs 257, is an embodiment wherein the sample is exposed to a plurality of light intensities. The intensity of the light source 120 will be selected to provide light output to the light detector 80 which will give optimal S/N data in the desired spectral region. In a first pass a light source, e.g., a lower intensity light source, is used to illuminate the sample, e.g. apple, to obtain data, with an acceptable S/N ratio, in the 700–925 nm region. At higher (>925 nm) and lower (<700 nm) wavelengths, the spectrum is dominated by noise due to the low light levels and is not useful. In a second pass a higher intensity light source is selected to illuminate the sample, saturating the detector array at the 700–925 nm regions while obtaining data with an acceptable S/N ratio, in the red pigment region of 500–600 nm, the chlorophyll region of 600–699 nm and in the O—H region of 926–1000 nm. The data from each of the two passes comprises separate data inputs delivered to an analog to digital converter for computer processing. Same spectrometer and A/D for benchtop unit, where the two spectra are acquired sequentially. For on-line, two spectrometers are used, each with its own A/D. In one embodiment A/D cards external to the computer are utilized which are serial and are provided by Ocean Optics. This process is provides for multiple channels into a data analyzer for analysis by software. In this embodiment Ocean Optics drivers, hereafter referred to as drivers, accept MS "C" or Visual Basic to 1) determine the spectrum detected from the sample or 2) subject the data to the predictive algorithm and produce the output. Display control computer programs or software periodically requests drivers to deliver the spectrums to be combined. The digital combination then produces, with standard display software, the output display representing the entire spectrum ranges detected from the each sample. There may be, for each sample, multiple spectrum data. For example the spectrum sampling protocol may seek 50 spectrum samples during each of the multiple passes, e.g., 50 spectrum samples during the pass subjecting the fruit sample to the lower intensity light source and separately 50 spectrum samples during the pass subjecting the fruit sample to the higher intensity light source. The total duration of each pass will be determined by the speed of the sorting/packing line and may be limited to approximately 5 ms per sample. However, it will be recognized, for all embodiments and sample types, that other sampling times and strategies will be within the realm of use for the invention disclosed herein as different samples and different embodiments are employed. Where the samples being processed, on a sorting/packing line, are apples, there is expected to be little space between each successive apple. Spectrum obtained from the space between apples and at the leading and trailing sides of the sample or apple will be discarded. As the sample, i.e., apple or other fruit, moves under the light detector 80, the spectrum data detected will be that exiting the sample 30 representative of the portion of the sample 30 constituting the path between the point of exposure of the sample 30 with the light source 120 and the point of spectrum exit for detection by the light detector 80. By mathematical inspection of each spectrum, e.g., automated inspection via a computer, this method can determine whether light detected by the light detector 80 is from an apple or the empty space between apples in a sorting/packing line sample conveyor 295. This method can also detect the leading and trailing edges of an apple as it passes by the light detector 80 having an output 82 to a spectrometer 170. From this data, discrimination can occur to select specific spectra samples which, for example, are expected to be from the midsection of the sample or apple. Using mathematical inspection of each spectrum (on-line) to determine if it is a good apple spectrum or a spectrum of the line material. The cycle detected by the light detector 80 thus, for each sample 30 in the on the sample conveyor 295 of a sorting/packing line, is composed of an initial segment where the light detector 80 or pickup fiber is exposed to only ambient light with a light shield 284 between the light detector 80 and the light source 120. As the sample 30, e.g., apple, moves into contact with and under the light shield 284, which may for example be a curtain 285, the leading edge or side of the apple will commence to be revealed permitting the light detector 80 to detect spectrum output 82 from the apple. Continued movement of the sample 30 under the light shield 284 exposes the light detector 80 to spectrum output 82 from the sample 30 until the sample 30 moves to the point where the trailing edge or side of the sample 30 is remaining exposed to the light source 120. The sample 30 then moves past the light shield 284 and all light from the light source 120 is blocked between the light detector 80 and the light source 120. Thus the initial spectra detected by the light detector 80 will be at the leading edge or side of the sample 30 as it approaches the curtain 285. The intermediate spectrum measurements, between the initial time at which the leading edge of the sample 30 is exposed to the light source 120 and the time when the trailing edge or side of the sample 30 is exposed to the light source 120, will include those where the light detector 80 or light pickup is optimally positioned to detect spectra most representative of the characteristics of the light spectra output 82 from the sample 30 as the light source 120 illuminates the sample 30, e.g., apple, other fruit or other O—H, C—H or N—H materials. In the preferred embodiment, for ease of data processing, the light detector 80 analog output 82 is converted to digital data by an A/D card. Computer program or software tests the data for acceptance or discarding. The criteria for acceptance of each spectrum sample 30 is a predetermined spectral feature determined by the expected spectral output 82 of the sample 30, e.g., where the sample 30 is an apple, i.e., the criteria will be to detect a spectrum from 250 to 1150 nm falling within the spectra expected for an apple. The detection of the space between apples, in the sorting/packing line, will be recognized as not apples. This spectrum acquired for each sample 30 is the input to the predictive algorithms as indicated by the flow diagram of FIG. 1C. Multiple spectrum, for example fifty spectrum, are detected by the light detector 80 for each sample. The computer program compares each detected discrete spectrum with an expected spectrum from the particular sample, the spectrum not meeting the criteria are discarded, the retained spectrum, e.g., 40–50 samples, are combined to provide the spectrum which becomes the input for the predictive algorithm. Multiple spectra from the same apple are averaged to provide a single average spectrum representing multiple points on the apple. the apple may be spinning as it travels by the sensor, e.g., clockwise or counter clockwise in relation to the direction of sorting line travel with better measurement indicated with counter-clockwise motion of the sample, thus giving even greater coverage of its surface. Once the average absorbance spectrum for a sample is calculated, the spectrum is multiplied by the regression vector (via a vector multiplication dot product). The regression vector is obtained from previous calibration efforts and is stored on the computer. There is a separate regression vector for each parameter being predicted—e.g., firmness, Brix. The results of the processing the spectrum output 82 by the predictive algorithms will determine the predicted characteristics of the sample 30. The characteristics determined for each discrete sample 30, e.g., apple or other fruit, will be used for decision making in handling or disposition of the sample 30 including, for example, 1) in the packing/sorting line different characteristics will be used for sorting and packing decisions, e.g., by color, size, firmness, taste as predicted by acidity and Brix and 2) characteristics indicating spoilage may trigger methods of elimination of the particular sample 30 from the packing/sorting line.

Packing and sorting of apples will likely involve multiple packing/sorting illumination or light source 120 and light detector 80s for each line. Where the sample 30 is comprised of smaller fruit, e.g., cherries or grapes, there may be multiple light sensors with single or multiple light to interrogate or examine and gather data from a tray of such smaller fruit rather than on the basis of examination of each discrete cherry or grape. For each sample 30, data is acquired, tested to determine if the data corresponds to preset criteria with data selected which meets preset criteria and discarded if it fails to meet preset criteria. Data received by light sensors is then combined to compose the total spectrum sampled. The total spectrum is then compared with the predictive algorithm and decisions are made regarding the sample 30 including, for example, sorting/packing decisions. The results of the comparison of the total spectrum with the predictive algorithm provides a number or other output for end use including information for computer directed sorting equipment.

Operation of the light source 120 is enables the rapid acquisition of reproducible data with good S/N, even in the highly light scattering and absorbing 250–699 nm and the strongly absorbing >950 nm region. The lamp 123 in the preferred embodiment is a 12-Volt, 75-Watt tungsten halogen lamp. However, other light sources which may be used include but are not limited to light emitting diode, laser diode, tunable diode laser, flash lamp and other such sources which will provide equivalent light source and will be familiar to those practiced in the art. The lamp is held at a resting voltage of 2-Volts. When a measurement is taken, the lamp is ramped up to the desired voltage, a brief delay allows the lamp output 82 to stabilize, then spectra are acquired. After data acquisition, the lamp is ramped down to the resting voltage. This procedure extends lamp life and prevents burning the sample. In high speed operations the lamp may always be lighted, e.g., on a high-speed packing/sorting line or used on harvest equipment, and a light "chopper" or shutter or other equivalent article or method could be utilized to deliver light to the passing sample for a determined period of time. The operation of the light source is important in extending lamp life, reducing operating expense and reducing disruption of operations. The lamp 123 voltage is ramped up and down to preserve lamp 123 life and to lessen the likelihood of burning fruit. A standby voltage to keeps the lamp 123 filament warm. An ambient/room light background measurement is made to correct for the dark spectrum, which may include ambient light. It is stored and subtracted from the sample and reference (if applicable) so that there is no contribution of ambient light to the sample spectrum, which would affect accuracy. Dual intensity illumination is employed to: 1) improve data accuracy above 925 nm and below 700 nm and 2) to normalize path length changes due to scattering. Dual exposure time increases the likelihood of increased data quality with large and small fruit. Utilization of more than one light detector 80, with each positioned at different distances from the sample, will likewise increase the ability to obtain increased data quality throughout each portion of the spectrum from approximately 250 nm to 1150 nm.

Other steps in determining predictive algorithms included reference determination of pH using electrode measurement and reference determination of total acidity using end-point titration of extracted juice. Correlation between the NIR spectra and the reference data (pH and total acidity) was conducted. Methods known to those practiced in the art such as partial least squares (PLS) are used to determine the correlation of the NIR spectrum with a chosen parameter such as pH. Once correlation is established, PLS is used to generate a regression vector from the calibration samples. This regression vector is then used to predict sample properties by taking the dot product of the sample spectrum and regression vector. NIR analysis can be carried our directly on the juice yielding very high correlations with Brix, pH, and total acidity. A commercially available "dip probe" is used that is a common item available from optical fiber fabricators or from companies involved in process analysis. In addition to the use of PLS for quantifying Brix, firmness, pH and acidity, Principal Components Analysis (PCA) was performed on the NIR spectral data. PCA differs from PLS in that no reference data is required. PCA allows classification of firm vs. soft apples and low pH vs. high pH samples. This classification algorithm is sufficient to achieve the goal of product segregation. Using PCA, poor quality fruit can be removed from a batch and the highest quality fruit can be segregated into a premium class. Poor quality fruit was observed to often have a higher pH level than good quality fruit.

FIG. 4 illustrates an alternative embodiment of the disclosure and includes at least one light source 120 transmitted by a transmitting article, for example a fiber optic fiber or other equivalent article for transmitting light; a sample 30 having an sample surface 35; input mechanism of positioning light from the at least one light source 120 proximal the sample surface; at least one illumination detector; output mechanism of positioning the at least one illumination detector proximal the sample surface; the at least one light source 120 and the at least one illumination detector may be positioned in relation to the surface or against the surface by a positioning article provided, for example, by a positioning article spring biased against the surface of the sample; the pressure against a sample surface, by an at least one light source 120 or an at least one illumination detector, will be limited by surface characteristics of the sample and/or the character of the measurement process, i.e., pressure may be reduced where a sample is subject to surface damage or where the measurement process is in at high speed limiting the time permitted for each separate sample contact. The illumination is transmitted to the surface, for example by fiber optics or other equivalent manner; and at least one device or method of measuring the illumination detected from the sample. The light source, for the disclosure herein may be a broadband lamp, which for example, but without limitation, may be a tungsten halogen lamp or the equivalent, which may produce a spectrum within the range 250–1150 nm and have a filament temperature of of 2500 to 3500 degrees kelvin; other broadband spectrum lamps may be employed depending upon the sample 30, characteristics to be predicted, and embodiment utilized; the at least one device or method of measuring the illumination may be a spectrometer having at least one input; the at least one spectrometer may include, for example, a 1024 linear array detector with those of ordinary skill in the art recognizing that other such detectors will provide equivalent detection; the at least one illumination detector may be a light pickup fiber or other equivalent detector including for example a fiber optics light pickup; the at least one illumination detector collects a spectrum which is received by the at least one spectrometer input; the sample in this embodiment is from the chemical group of CH, NH, OH or the physical characteristics of firmness, density, color and internal and external defects. Additionally, the light source 120 may comprises a plurality of illumination fibers. In this embodiment a plurality of illumination fibers may be arrayed such that each of the plurality of illumination fibers is equidistant from adjacent illumination fibers; the at least one illumination detector may, in this embodiment, be positioned centrally in the array of illumination fibers. In an embodiment of this disclosure, the plurality of illumination fibers may, for example, be comprised of 32 illumination fibers and the light source 120 may be provided, for example, by a 5 w tungsten halogen lamp or other equivalent light source or by a plurality of illumination sources provided for example by at least two light sources such as, for example, at least two 50 Watt light sources. Illumination sources may be composed, for example, of sources having a focusing ellipsoidal reflector with cooling fan. In this embodiment the at least one illumination detector may comprise a plurality of light detectors 80, which may for example, be arrayed such that each illumination detector is equidistant from adjoining light detectors 80; where at least two light sources are positioned are employed, they may for example be positioned 45 degrees relative to the illumination detectors. in the array of illumination fibers. In an additional embodiment of this disclosure, a plurality of light detectors 80 may be comprised of twenty-two illumination detectors. An embodiment of the disclosure may be comprised of at least one light source 120 composed of a 5 w tungsten halogen lamp; the at least one illumination detector is a single detection fiber; the light source 120 is positioned against the sample 30 degrees distal to the detection fiber. If the measurement of the sample surface is made in a non-contacting manner, an alternative embodiment may include a polarization filter between the light source 120 and the sample, provided, for example by a linear polarization filter or an equivalent as understood by one of ordinary skill in the art; a matching polarization filter is positioned between the at least one illumination detector and the sample, which may be provided, for example by a linear polarization filter rotated 90 degrees in relation to the polarization filter between the light source 120 and the sample.

The method described above, which uses wavelengths of both visible radiation (250–699 nm) specifically chosen to include the absorption band for yellow color pigments (250–499 nm), red color pigments (500–600 nm) and green pigments or chlorophyll (601–699 nm), as well as NIR (700–1150 nm) radiation to correlate with Brix, firmness, pH, acidity, density, color and internal and external defects can be carried out using a variety of apparatuses.

While a preferred embodiment of the present disclosure has been shown and described, it will be apparent to those skilled in the art that many changes and modifications may be made without departing from the disclosure in its broader aspects. The appended claims are therefore intended to cover all such changes and modifications as fall within the true spirit and scope of the disclosure.

I claim:

1. A method of determining characteristics of samples comprising:
   A building algorithms of the relationship between sample characteristics and absorbed and scattered light from a sample having an interior;
   B illuminating the interior of a sample with a broadband frequency spectrum;
   C detecting the spectrum of absorbed and scattered light from the sample;
   D analyzing the detected spectrum of absorbed and scattered light from the sample with the algorithms; calculating the characteristics of the sample.
2. The method of claim 1 further comprising:
   A building the algorithms to generate a regression vector that relates the frequency spectrum, further comprised of VIS and NIR spectra, to brix, firmness, acidity, density, pH, color and external and internal defects and disorders;
   B storing the regression vector, in a CPU having a memory, as a prediction or classification calibration algorithm;
   C illuminating the sample interior with a spectrum of 250 to 1150 nm;
   D inputting the detected spectrum of absorbed and scattered light from the sample interior to a spectrometer;
   E converting the detected spectrum from analog to digital and inputting the converted spectrum to a CPU; combining the spectrum detected;
   F comparing the combined spectrum with a stored calibration algorithm;
   G predicting the characteristics of the sample.
3. The method of claim 1 further comprising:
   A the characteristics are chemical characteristics including acidity, pH and sugar content.
4. The method of claim 1 further comprising:
   A the characteristics are physical characteristics including firmness, density, color, appearance and internal and external defects and disorders.
5. The method of claim 1 further comprising:
   A the characteristics are consumer characteristics.
6. The method of claim 1 further comprising:
   A sampling is of samples from the group of C—H, N—H or O—H chemical groups;
   B illuminating of the interior of the sample is with a frequency spectrum including visible and near infrared light;
   C building algorithms for a correlation analysis separately of Brix, firmness, ph and acidity in relation to the light spectrum output from the illuminated sample;
   D detecting the spectrum of absorbed and scattered light from the sample with a light detector.
7. The method of claim 2 further comprising:
   A illuminating of the interior of the sample with a frequency spectrum of 250 to 1150 nm;
   B detecting the spectrum with a light detector fiber; shielding the light detector fiber from the illuminating spectrum;
   C measuring the spectrum for chlorophyl at around 680 nm;
   D correlating the characteristics of Brix, firmness, pH and acidity with the measured spectrum.
8. An apparatus for determining characteristics of samples comprising;
   A at least one broadband light source; a sample having an sample surface and an interior; input mechanism of positioning the at least one light source proximal the sample surface;
   B at least one light detector; output mechanism of positioning the at least one light detector proximal the sample surface;
   C at least one mechanism of measuring the illumination detected from the sample;
   D the at least one light source produces a spectrum within the range of 250 to 1150 nm;
   E the at least one mechanism of measuring the illumination is a spectrometer; the spectrometer has at least one input;
   F the at least one light detector is a light pickup fiber; the at least one light detector collects a spectrum which is received by the at least one spectrometer input;
   G the sample is from the chemical group consisting of C—H, N—O, and O—H.
9. The apparatus of claim 8 further comprising:
   A the least one light source is a tungsten halogen lamp; the illumination is transmitted to the sample surface by fiber optics;

B the at least one light detector is a fiber optics light pickup;

C the at least one spectrometer comprises a 1026 linear array detector.

10. The apparatus of claim 8 further comprising:

A the at least one light source is an illumination fiber.

11. The apparatus of claim 8 further comprising:

A the at least one light source comprises a plurality of illumination fibers;

B the plurality of illumination fibers are arrayed such that each illumination fiber is equidistant from adjoining illumination fibers; the at least one light detector is positioned centrally in the array of illumination fibers.

12. The apparatus of claim 11 further comprising:

A the plurality of illumination fibers are comprised of 32 illumination fibers.

13. The apparatus of claim 8 further comprising:

A the light source is a 5 w tungsten halogen lamp.

14. The apparatus of claim 8 further comprising:

A the at least one light source comprises a plurality of light sources which is further comprised of two 50 w light sources;

B the at least one light detector is comprised of a plurality of light detectors.

15. The apparatus of claim 14 further comprising:

A the plurality of light detectors are arrayed such that each light detector is equidistant from adjoining light detectors.

16. The apparatus of claim 15 further comprising:

A the plurality of light detectors comprise twenty-two light detectors.

17. The apparatus of claim 9 further comprising:

A the light source comprised of an ellipsoidal reflector with a 50 w bulb with cooling fan; the fiber optics is comprised of at least one fiber optic fiber for transmission of the light source to the sample surface.

B the at least one fiber optic and the at least one light detector spring biased against the sample surface; the pressure exerted by the spring biasing limited by the character of the sample.

18. The apparatus of claim 8 further comprising:

A the at least one light source is a 5 w tungsten halogen lamp; the at least one light detector is a single fiber optic fiber; the illumination source is positioned against the sample surface 180 degrees distal to the detection fiber.

19. The apparatus of claim 11 further comprising:

A a polarization filter is positioned between the at least one light source and the sample;

B a matching polarization filter is positioned between the at least one light detector and the sample.

20. The apparatus of claim 19 further comprising:

A the polarization filter is a linear polarization filter; the matching polarization filter is a linear polarization filter rotated 90 degrees in relation to the polarization filter.

\* \* \* \* \*